US010415047B2

(12) United States Patent
Dale et al.

(10) Patent No.: US 10,415,047 B2
(45) Date of Patent: *Sep. 17, 2019

(54) TABV TRANSCRIPTIONAL CONTROL ELEMENTS, CHIMERIC CONSTRUCTS AND USES THEREFOR

(71) Applicants: James Langham Dale, Queensland (AU); Robert Maxwell Harding, Queensland (AU); Douglas Kenneth Becker, Queensland (AU); Gregory John Hafner, Queensland (AU); Ilin Yang, Queensland (AU)

(72) Inventors: James Langham Dale, Queensland (AU); Robert Maxwell Harding, Queensland (AU); Douglas Kenneth Becker, Queensland (AU); Gregory John Hafner, Queensland (AU); Ilin Yang, Queensland (AU)

(73) Assignee: Farmacule Bioindustries Pty Ltd, Kelvin Grove (AU)

(*) Notice: Subject to any disclaimer, the term of this patent is extended or adjusted under 35 U.S.C. 154(b) by 0 days.

This patent is subject to a terminal disclaimer.

(21) Appl. No.: 15/194,766

(22) Filed: Jun. 28, 2016

(65) Prior Publication Data
US 2018/0105821 A1    Apr. 19, 2018

Related U.S. Application Data

(60) Continuation of application No. 12/570,431, filed on Sep. 30, 2009, now Pat. No. 9,413,365, which is a division of application No. 10/521,571, filed as application No. PCT/AU03/00919 on Jul. 17, 2003, now Pat. No. 7,598,366.

(60) Provisional application No. 60/396,912, filed on Jul. 17, 2002.

(51) Int. Cl.
*C12N 15/82*    (2006.01)
*C07K 14/005*    (2006.01)

(52) U.S. Cl.
CPC ........ *C12N 15/8216* (2013.01); *C07K 14/005* (2013.01); *C12N 15/8222* (2013.01); *C12N 15/8223* (2013.01); *C12N 2730/00022* (2013.01)

(58) Field of Classification Search
None
See application file for complete search history.

(56) References Cited

U.S. PATENT DOCUMENTS

| 6,391,639 | B1 | 5/2002 | Schenk et al. | |
|---|---|---|---|---|
| 7,598,366 | B2* | 10/2009 | Dale | C07K 14/005 435/419 |
| 9,416,365 | B2* | 8/2016 | Dale | C07K 14/005 |

FOREIGN PATENT DOCUMENTS

| WO | WO 99/00492 | 1/1999 |
|---|---|---|
| WO | WO 99/09190 | 2/1999 |
| WO | WO 99/43836 | 9/1999 |

OTHER PUBLICATIONS

Benfey et al., Science 250: 959-966 (1990).
Bhattacharyya-Pakrasi et al., The Plant Journal 4(1): 71-79 (1993).
Couhida et al., J. Gen Virol. 74(1): 15-22 (1993), GenPept Acession AAA47454.
Donald et al., The EMBO Journal 9: 1717-1726 (1990).
Geijskes et al., Sequence Analysis of an Australian Isolate of Sugarcane Bacilliform Badnavirus (2001), GenBank Acession AJ277091.
Hagen et al., Virology 196(2): 619-628 (1993), GenBank Accession L14546.
Hagen et al., Virology 196(2): 619-628 (1993), GenPept Accession AAA03169.
Harper et al., Virus Genes 17(3): 271-278 (1998).
Huang et al., J. Gen. Virol. 82(10): 2549-2558 (2001), GenPept Accession AAL18494.
Huang et al., GenBank Accession NP 569153, pp. 1-2 (2001).
James et al., J. Gen. Virol. 21: 145-153 (1973).
Kim et al., Plant Molecular Biology 24: 105-117 (1994).
Klöti et al., Plant Molecular Biology 40: 249-266 (1999).
Lockhart et al., Breeding Banana and Plantain for Resistance to Diseases and Pests 105-113, CIRAD/INIBAP (1993).
Lockhart et al., Virus Taxonomy 185-188, Springer-Verlag/Wien (1995).
Medberry et al., The Plant Cell 4: 185-192 (1992).
Medberry et al., Nucleic Acids Research 18(18): 5505-5513 (1990).
Schenk et al., Plant Molecular Biology 39: 1221-1230 (1999).
Tzafrir et al., Plant Molecular Biology 38: 347-356 (1998).
Yang et al., Plant Cell Rep 21: 1199-1206 (2003).
Yang et al., Arch Virol 148: 937-949 (2003).
Yang et al., Arch Virol 148: 1957-1968 (2003).

* cited by examiner

*Primary Examiner* — Cynthia E Collins
(74) *Attorney, Agent, or Firm* — Perkins Coie LLP

(57) ABSTRACT

This invention discloses a constitutive promoter from the Taro bacilliform virus (TaBV) for expression of foreign or endogenous coding sequences in plants, including dicotyledonous and monocotyledonous plants. The invention also discloses a chimeric nucleic acid construct comprising the promoter of the invention operably linked to a foreign or endogenous polynucleotide that codes for a protein of interest or a transcript capable of modulating expression of a target gene. The invention further discloses transformed plant cells, as well as differentiated plants and plant parts, containing the construct. Methods for diagnosis and treatment of viral infections, especially badnaviral infections, are also disclosed.

29 Claims, 9 Drawing Sheets

Specification includes a Sequence Listing.

TABV TRANSCRIPTIONAL CONTROL ELEMENTS, CHIMERIC CONSTRUCTS AND USES THEREFOR

This application is a continuation of Ser. No. 12/570,431 (allowed) filed Sep. 30, 2009, which is a divisional of U.S. application Ser. No. 10/521,571 filed May 16, 2005, which is a 371 of PCT/AU2003/000919 filed Jul. 17, 2003, which claims priority to U.S. Provisional App. No. 60/396,912 filed Jul. 17, 2002, the entireties of which are hereby incorporated by reference.

FIELD OF THE INVENTION

THIS INVENTION relates generally to transcriptional control elements for use in plant genetic engineering. More particularly, the present invention relates to a constitutive promoter for expression of foreign or endogenous coding sequences in plants, including dicotyledonous and monocotyledonous plants. The invention is also concerned with a chimeric nucleic acid construct comprising the promoter of the invention operably linked to a foreign or endogenous polynucleotide that codes for a protein of interest or a transcript capable of modulating expression of a target gene. The invention is further concerned with transformed plant cells, as well as differentiated plants and plant parts, containing the construct.

BACKGROUND OF THE INVENTION

A primary goal of genetic engineering is to obtain plants having improved characteristics or traits. Many different types of characteristics or traits are considered advantageous, but those of particular importance include resistance to plant diseases, resistance to viruses or insects and resistance to herbicides. Other advantageous characteristics or traits include tolerance to cold or soil salinity, enhanced stability or shelf life of the ultimate consumer product obtained from a plant, or improvement in the nutritional value of edible portions of a plant.

Recent advances in genetic engineering have enabled the incorporation of a selected gene (or genes) into plant cells to impart a desired quality (or qualities) to a plant of interest. The selected gene (or genes) may be derived from a source different from the plant of interest or may be native to the desired plant, but engineered to have different or improved qualities. This new gene (or genes) may then be expressed in cells of the regenerated plant to exhibit the new trait or characteristic.

In order for the newly incorporated gene to express the protein for which it codes in a plant cell, the proper regulatory signals must be present, in the proper location with respect to the gene. These regulatory signals include a promoter, a 5' non-translated leader sequence and a 3' polyadenylation signal.

The efficiency of gene expression is governed largely by the promoter used to express the gene. A promoter is typically a DNA sequence that directs the cellular machinery of a plant to produce (transcribe) RNA (transcript) from a contiguous transcribable region downstream (3') of the promoter. The promoter influences the rate at which the transcript of the gene is made. Assuming the transcript includes a coding region with appropriate translational signals, the promoter also influences the rate at which the resultant protein product of the gene is produced. Promoter activity also can depend on the presence of several other cis-acting regulatory elements which, in conjunction with cellular factors, determine strength, specificity, and transcription initiation site (for a review, see Zawel and Reinberg, 1992, *Curr. Opin. Cell Biol.* 4: 488).

It has been shown that certain promoters are able to direct RNA synthesis at a higher rate relative to other promoters. These are called "strong promoters". Certain other promoters have been shown to direct RNA production at higher levels only in particular types of cells or tissues and are often referred to as "tissue-specific promoters". Promoters that are capable of directing RNA production in many or all tissues of a plant are called "constitutive promoters". Thus, expression of a chimeric gene (or genes) introduced into a plant may potentially be controlled by identifying and using a promoter with the desired characteristics.

There have been numerous promoters described for gene expression in dicotyledonous plants. However, there still remains a dearth of promoters that can be used for effective expression of foreign or endogenous coding sequences in monocotyledonous plants.

One promoter that has been used widely for directing gene expression in, especially, dicotyledonous plants, is the 35S promoter derived from cauliflower mosaic virus (CaMV), a member of the family Caulimoviridae. CaMV is the source for both the 35S and 19S promoters, but the 35S promoter has been most widely used. It is capable of directing strong, constitutive expression in many dicotyledonous species and is generally functional, albeit with somewhat reduced activity, in monocotyledonous plants (Benfey and Chua, *Science* 244:174-181, 1989; *Science* 250: 959-966, 1990; Fang et. al., *Plant Cell* 1:141-150, 1989; Fütterer et al., *EMBO J* 9: 1697-1707, 1990; Terada and Shimamoto, *Mol. Gen Genet* 220:389-392, 1990).

In addition to the caulimoviruses, promoters have also been isolated from several badnaviruses including Commelina yellow mottle virus, banana streak virus and sugarcane bacilliform virus. *Badnaviruses* are pararetroviruses, also classified in the family Caulimoviridae, genus *Badnavirus*. They have bacilliform-shaped virions approximately 30×130 nm encapsidating a circular dsDNA genome ranging from 7.1-7.6 kbp that contains three open reading frames (ORF's) (Lockhart B. E. L. and Olszewski N. E. in Ganry J. (ed). *CIRAD/INIBAP*, Montpellier, 1993, pp. 105-113; Lockhart et al., (eds). *Virus Taxonomy: Sixth Report of the international Committee on the Taxonomy of Viruses*. Springer, Wien, 1995, pp. 185-188; Medberry et al., *Nucleic Acids Research* 18:5505-5513, 1990.). Badnaviruses have been reported to infect a wide range of tropical plant species, including economically important monocotyledonous crops such banana, sugarcane and rice.

Nevertheless, despite the existence of these representative promoters, there remains a need to identify promoter sequences with improved efficacy and efficiency in directing the expression of heterologous DNA sequences in all plant species and, in particular, in monocotyledonous plants.

SUMMARY OF THE INVENTION

The present invention is predicated in part on the recent sequencing, characterisation and classification of a Papua New Guinea isolate of Taro bacilliform virus (TaBV), which is associated with Alomae disease of taro (*Colocasia esculenta*), as a badnavirus, based on its non-enveloped, bacilliform virion morphology and transmission by mealybugs. The promoter region of this badnavirus, in particular, has been found quite unexpectedly to direct constitutive gene expression not only in dicotyledonous plant species but also in monocotyledonous plants, especially non-graminaceous monocotyledonous plants. The foregoing discovery has been reduced to practice in novel isolated DNA molecules, promoter regions, chimeric DNA constructs as well as plant cells and differentiated plants containing them, as described hereinafter.

Thus, in one aspect, the present invention provides an isolated DNA molecule comprising a promoter or biologically active fragment thereof or variant of these, wherein the promoter is located upstream of a transcribable DNA sequence that hybridises to a nucleic acid probe derived from the polynucleotide sequence set forth in SEQ ID NO:1.

Advantageously, the isolated promoter is of sufficient length such that it is capable of initiating and regulating transcription of a DNA sequence to which it is coupled. The promoter may be between about 250 nucleotides (nts) and 1200 nts in length and usually greater than 500 nts in length.

An analogous promoter can be obtained from an organism, especially from a virus, and more especially from a badnavirus, which has a DNA sequence that is capable of hybridising to a nucleic acid probe derived from the sequence set forth in SEQ NO:1 under at least low stringency conditions, especially under at least medium stringency conditions, and more especially under high stringency conditions.

The polynucleotide sequence set forth in SEQ ID NO:1 is a transcribable DNA sequence comprising three ORFs of the badnavirus, Taro bacilliform virus (TaBV). Such viruses are highly transcribed in tissue of infected monocotyledonous plants. Accordingly, nucleotide sequences that correspond or are complementary to at least a portion of the sequence set forth in SEQ ID NO:1 may be useful as probes for isolating homologous transcribable sequences from other organisms, especially from other viruses and more especially from other badnaviruses to, in turn, permit the isolation from those other organisms of promoters with analogous qualities to those described herein. In addition, these nucleotide sequences and their encoded amino acid sequences may be useful in diagnostic applications for detecting the presence of infecting virus particles in plants such as, for example, taro plants, e.g. using detectable agents which interact specifically with those nucleotide or amino acid sequences. Thus, in another aspect, the invention provides an isolated polynucleotide comprising a nucleotide sequence that corresponds or is complementary to at least a portion of the sequence set forth in SEQ ID NO:1 or to a variant thereof. The variant suitably displays at least 30, 40, 50, 60, 70, 80, 90, 95% sequence identity to at least a portion of the sequence set forth in SEQ ID NO:1. Desirably, the variant hybridises to at least a portion of the sequence set forth in SEQ ID NO:1 under at least low stringency conditions, more desirably under at least medium stringency conditions, and even more desirably under high stringency conditions. Portions of SEQ ID NO:1, which are contemplated by the present invention, are suitably at least 18, 19, 20, 21, 22, 23, 24, 25, 26, 27, 28, 29, 30, 40, 50 ,60 , 70, 80, 90, 100, 120, 140, 160, 180, 200, 250, 300 nucleotides in length.

In yet another aspect, the invention provides an isolated polypeptide comprising an amino acid sequence that corresponds to at least a portion of the sequence set forth in any of SEQ ID NO:3, 4 or 5, or of a variant that displays at least 30, 35, 40, 45, 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence identity to that sequence.

In some embodiments, the promoter comprises the sequence set forth in SEQ ID NO:6. In this embodiment, a biologically active fragment of the promoter is suitably selected from any one of the sequences set forth in SEQ ID NO:7, 8 and 9.

In some embodiments, a variant of the promoter has at least 30, 35, 40, 45, 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence identity to any one of the polynucleotides identified by SEQ ID NO:6, 7, 8 and 9. In another embodiment, a variant of the promoter is capable of hybridising to any one of the polynucleotides identified by SEQ ID NO:6, 7, 8 and 9 under at least low stringency conditions, especially under at least medium stringency conditions, and more especially under high stringency conditions.

Suitably, a promoter of the invention can be fused to a desired coding sequence to create a chimeric construct. This construct can then be introduced into a host cell, typically a plant cell or plant or plant part, by any method of choice. Accordingly, in another aspect of the invention, there is provided a chimeric DNA construct comprising an isolated promoter or biologically active fragment thereof or variant of these, wherein the promoter is naturally located upstream of a transcribable DNA sequence which hybridises to a nucleic acid probe derived from the polynucleotide sequence set forth in SEQ ID NO:1, wherein the promoter or biologically active fragment or variant is operably linked to a foreign or endogenous DNA sequence to be transcribed.

Suitably, the chimeric DNA construct further comprises a 3' non-translated sequence that is operably linked to the foreign or endogenous DNA sequence and that functions in plant cells to terminate transcription and/or to cause addition of a polyadenylated nucleotide sequence to the 3' end of a transcribed RNA sequence.

The foreign or endogenous DNA sequence is foreign or endogenous with respect to the plant cell in which it is or will be introduced. In some embodiments, the foreign or endogenous DNA sequence encodes a structural or regulatory protein, or alternatively, a transcript capable of modulating expression of a corresponding target gene. In some embodiments, the transcript comprises an antisense RNA or a ribozyme or other transcribed region aimed at downregulation of expression of the corresponding target gene. For example, the other transcribed region may comprise a sense transcript aimed at sense suppression co-suppression) of the corresponding target gene.

In some embodiments, depending upon the selected foreign or endogenous DNA sequence, the chimeric DNA construct may be further characterised in that the promoter or biologically active fragment or variant is capable of conferring transcription, especially high levels of transcription, of the foreign or endogenous DNA sequence in many or all tissues of a plant.

In still another aspect, the invention provides a method for expression of a foreign or endogenous DNA sequence, comprising introducing into a plant cell a chimeric DNA construct as broadly described above.

In a further aspect, the invention contemplates a method for producing a transformed plant cell, comprising introducing into a plant cell a chimeric DNA construct as broadly described above.

In still yet another aspect, the invention contemplates a method for producing transformed plant cells, comprising introducing into regenerable plant cells a chimeric DNA construct as broadly described above so as to yield transformed plant cells and identifying or selecting transformed plant cells.

In yet another aspect, the invention provides a method for selecting stable genetic transformants from transformed plant cells, comprising introducing into regenerable plant cells a chimeric DNA construct as broadly described above so as to yield transformed plant cells and identifying or selecting a transformed plant cell line from the transformed plant cells.

In some embodiments, the regenerable cells are regenerable dicotyledonous plant cells, usually monocotyledonous plant cells such as regenerable graminaceous monocotyledonous plant cells and especially regenerable non-graminaceous monocotyledonous plant cells. In some embodiments, the expression of the chimeric DNA construct in the transformed cells imparts a phenotypic characteristic to the transformed cells.

According to another aspect of the invention, there is provided a transformed plant cell containing a chimeric DNA construct as broadly described above.

In still another aspect, the invention contemplates a method for producing a differentiated transgenic plant, comprising introducing a chimeric DNA construct as broadly described above into regenerable plant cells so as to yield regenerable transformed cells, identifying or selecting a population of transformed cells, and regenerating a differentiated transgenic plant from the population.

In some embodiments, the expression of the chimeric DNA construct renders the differentiated transgenic plant identifiable over the corresponding non-transgenic plant.

In still a further aspect, the invention provides a differentiated transgenic plant comprising plant cells containing a chimeric DNA construct as broadly described above.

The chimeric DNA construct is transmitted through a complete cycle of the differentiated transgenic plant to its progeny so that it is expressed by the progeny plants. Thus, the invention also provides seed, other plant parts, tissue, and progeny plants derived from the differentiated transgenic plant.

The invention also extends to a method for diagnosing a badnaviral infection of a plant, comprising detecting the presence in a cell or tissue of the plant of (a) a nucleotide sequence that corresponds or is complementary to at least a portion of the nucleotide sequence set forth in SEQ ID NO:1 or 2, or of a variant of the nucleotide sequence, or (b) an amino acid sequence that corresponds to at least a portion of the sequence set forth in SEQ ID NO:3, 4 or 5, or of a variant of the amino acid sequence.

The badnaviral nucleic acid and amino acid sequences described herein can also be used to screen for drugs which modulate one or more of their activities, and which would be useful for the treatment and/or prevention of badnavirus infections. Thus, in yet another aspect of the invention there is provided a method of screening for an agent that modulates badnaviral infection, the method comprising:

contacting a preparation comprising:
(i) a polypeptide comprising an amino acid sequence that corresponds to at least a portion of the sequence set forth in SEQ ID NO: 3, 4 or 5, or of a variant of the sequence; or
(ii) a polynucleotide comprising a nucleotide sequence that corresponds or is complementary to at least a portion of the sequence set forth in SEQ ID NO:1 or 2, which polynucleotide is operably linked to a promoter; or
(iii) a polynucleotide comprising a reporter gene that is operably connected to a promoter comprising the sequence set forth in SEQ ID NO:6, 7, 8 or 9,
with a test agent; and
detecting a change in the level and/or functional activity of the polypeptide, or an expression product of the nucleotide sequence or of the reporter gene, relative to a normal or reference level and/or functional activity in the absence of the test agent.

In some embodiments, the agent inhibits or reduces badnavirus infection. In this instance, the method is further characterised by detecting a reduction in the level and/or functional activity of the polypeptide, or an expression product of the nucleotide sequence or of the reporter gene, relative to the normal or reference level and/or functional activity.

In another aspect, the invention provides a method for treating and/or preventing badnaviral infection of a plant, comprising administering to the plant an agent that:
reduces the level and/or functional activity of:
a polypeptide that comprises an amino acid sequence corresponding to at least a portion of the sequence set forth in SEQ ID NO: 3, 4 or 5, or of a variant of that sequence; or
an expression product of a nucleotide sequence that corresponds or is complementary to at least a portion of the sequence set forth in SEQ ID NO:1 or 2; or
reduces the functional activity of a promoter that comprises the sequence set forth in any one of SEQ ID NO:6, 7, 8 or 9.

BRIEF DESCRIPTION OF THE SEQUENCES: SUMMARY TABLE

TABLE A

Figure 1:
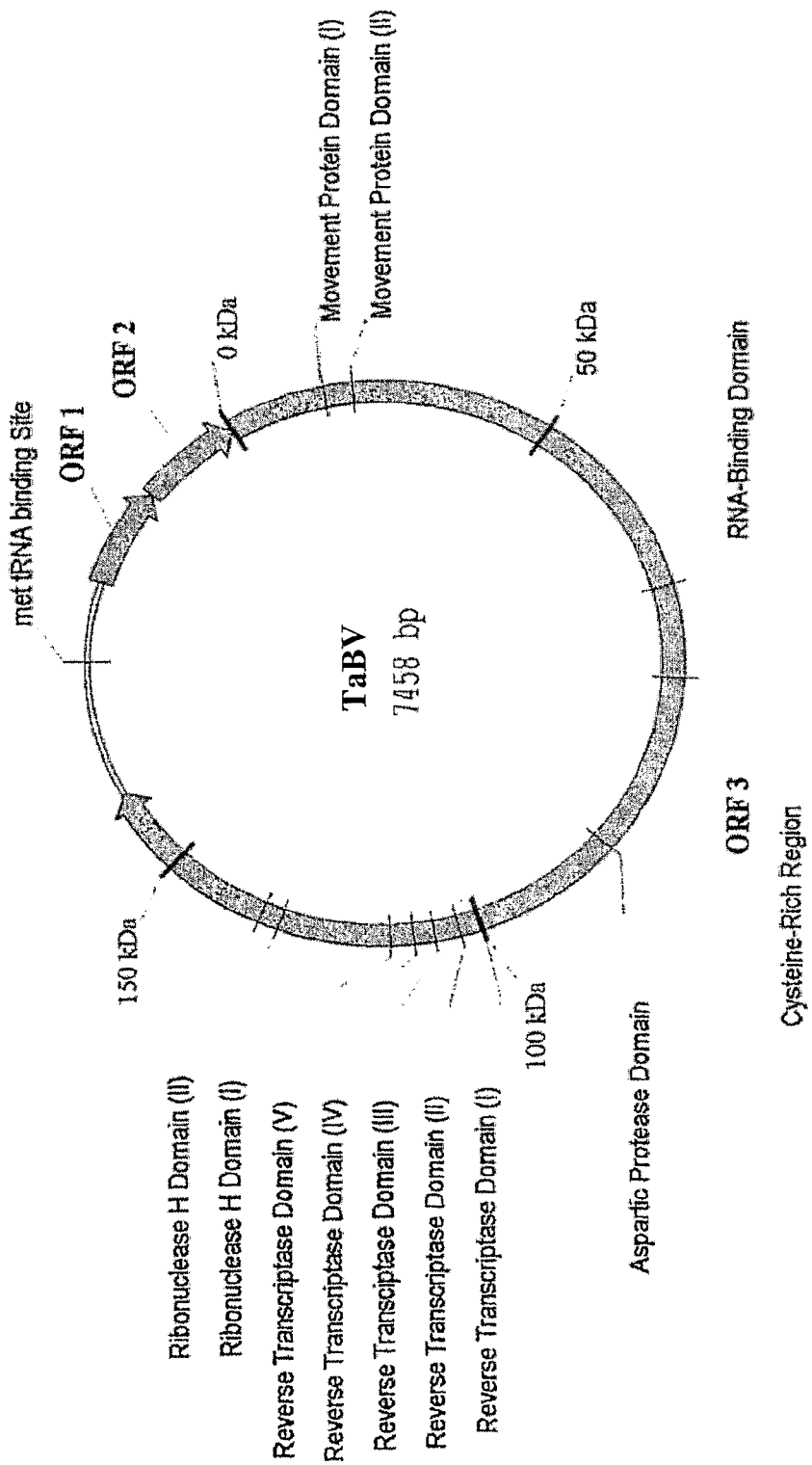
FIG. 1 is a diagrammatic representation of the genome organisation of TaBV. The positions of ORF 1, ORF 2, and ORF 3 are shown. The location of the putative met tRNA binding site, putative movement protein domains, RNA binding domain. (RB), cysteine-rich region, conserved aspartic protease domain, conserved reverse transcriptase domains and conserved RNAse H domains are indicated. Positions for designing primers Badna FP, Badna RP, TRBR, 5F (starts at nucleotide 7,344), IF (starts at nucleotide 5,534) and G2R (starts at nucleotide 5,556) are indicated by FP, RP, R, a, b, and c, respectively.

| Sequence ID Number | Sequence | Length |
| --- | --- | --- |
| SEQ ID NO: 1 | Genomic sequence of Papua New Guinea isolate of Taro bacilliform virus encoding ORFs 1, 2 and 3 | 6520 nts |
| SEQ ID NO: 2 | Entire genomic sequence of Papua New Guinea isolate of Taro bacilliform virus. | 7458 nts |
| SEQ ID NO: 3 | Putative Polypeptide product ORF 1, encoded by nucleotides 353-793 of SEQ ID NO: 1 | 146 aa |
| SEQ ID NO: 4 | Putative Polypeptide product ORF 2, encoded by nucleotides 792-1227 of SEQ ID NO: 1 | 144 aa |
| SEQ ID NO: 5 | Putative Polypeptide product ORF 3, encoded by nucleotides 1230-6872 of SEQ ID NO: 1 | 1881 aa |
| SEQ ID NO: 6 | Polynucleotide representing promoter region 6281-12, designated T1200 | 1190 nts |
| SEQ ID NO: 7 | Polynucleotide representing promoter region 6873-12, designated T600 | 598 nts |
| SEQ ID NO: 8 | Polynucleotide representing promoter region 6942-12, designated T500 | 529 nts |
| SEQ ID NO: 9 | Polynucleotide representing promoter region 7210-12, designated T250 | 261 nts |
| SEQ ID NO: 10 | Badna FP primer | 23 nts |
| SEQ ID NO: 11 | Badna RP primer | 24 nts |
| SEQ ID NO: 12 | IF primer | 23 nts |
| SEQ ID NO: 13 | TRBR primer | 26 nts |
| SEQ ID NO: 14 | 5F primer | 22 nts |
| SEQ ID NO: 15 | G2R primer | 25 nts |
| SEQ ID NO: 16 | cytoplasmic initiator methionine tRNA (tRNA$^{met}$) binding site | 12 nts |
| SEQ ID NO: 17 | E-GTN primer | 25 nts |
| SEQ ID NO: 18 | R-GTN primer | 24 nts |
| SEQ ID NO: 19 | P527-F primer | 20 nts |
| SEQ ID NO: 20 | P257-F primer | 23 nts |
| SEQ ID NO: 21 | P114-F primer | 23 nts |
| SEQ ID NO: 22 | FP-as-1 primer | 24 nts |
| SEQ ID NO: 23 | TRBR-Bam primer | 24 nts |
| SEQ ID NO: 24 | FP-6765-pro primer | 21 nts |
| SEQ ID NO: 25 | P600Not-F primer | 28 nts |
| SEQ ID NO: 26 | P600Bgl-R primer | 30 nts |

TABLE A-continued

| Sequence ID Number | Sequence | Length |
|---|---|---|
| SEQ ID NO: 27 | RP-leader primer | 27 nts |
| SEQ ID NO: 28 | GUS1 primer | 15 nts |
| SEQ ID NO: 29 | GUS2 primer | 12 nts | nts = nucleotides;
aa = amino acids

DETAILED DESCRIPTION OF THE INVENTION

1. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

The term "about" is used herein to refer to sequences that vary by as much as 30, 25, 20, 19, 18, 17, 16, 15, 14, 13, 12, 11, 10% to the length of a reference sequence.

"Amplification product" refers to a nucleic acid product generated by nucleic acid amplification techniques.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity.

As used herein, the term "binds specifically" and the like refers to antigen-binding molecules that bind the polypeptide or polypeptide fragments of the invention but do not significantly bind to homologous prior art polypeptides.

The term "biologically active fragment", as applied to promoter sequences, refers to a fragment that has at least about 0.1, 0.5, 1, 2, 5, 10, 12, 14, 16, 18, 20, 22, 24, 26, 28, 30% of the activity of a reference promoter sequence. It will also be understood that the phrase "biologically active fragment" refers to a part of an indicated DNA sequence that initiates RNA transcription or that, when fused to a particular gene and introduced into a plant cell, causes expression of the gene at a level higher than is possible in the absence of such part of the indicated DNA sequence. Included within the scope of the present invention are biologically active fragments of at least about 18, 19, 20, 21, 22, 23, 24, 25, 26, 27, 28, 29, 30, 40, 50 ,60 , 70, 80, 90, 100, 120, 140, 160, 180, 200, 250, 300 nucleotides in length. Alternatively, the term "biologically active fragment", as applied to polypeptides of the invention, includes deletion mutants and small peptides, for example of at least 6, 7, 8, 9, 10, 11, 12, 13, 14, 15, 16, 17, 18, 19, 20, 21, 22, 23, 25, 26, 27, 28, 29, 30 contiguous amino acid residues, which comprise an activity of a parent polypeptide.

The terms "chimeric construct" or "chimeric DNA" and the like are used herein to refer to a gene or DNA sequence or segment comprising at least two DNA sequences or segments from species which do not combine DNA under natural conditions, or which DNA sequences or segments are positioned or linked in a manner which does not normally occur in the native genome of the untransformed plant.

Throughout this specification, unless the context requires otherwise, the words "comprise", "comprises" and "comprising" will be understood to imply the inclusion of a stated step or element or group of steps or elements but not the exclusion of any other step or element or group of steps or elements.

"Constitutive promoter" refers to a promoter that directs expression of an operably linked transcribable sequence in many or all tissues of a plant.

By "corresponds to" or "corresponding to" is meant a polynucleotide (a) having a nucleotide sequence that is substantially identical or complementary to all or a portion of a reference polynucleotide sequence or (b) encoding an amino acid sequence identical to an amino acid sequence in a peptide or protein. This phrase also includes within its scope a peptide or polypeptide having an amino acid sequence that is substantially identical to a sequence of amino acids in a reference peptide or protein.

The terms "growing" or "regeneration" as used herein mean growing a whole, differentiated plant from a plant cell, a group of plant cells, a plant part (including seeds), or a plant piece (e.g., from a protoplast, callus, or tissue part).

"Hybridisation" is used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA U pairs with A and C pairs with G. In this regard, the terms "match" and "mismatch" as used herein refer to the hybridisation potential of paired nucleotides in complementary nucleic acid strands. Matched nucleotides hybridise efficiently, such as the classical A-T and G-C base pair mentioned above. Mismatches are other combinations of nucleotides that do not hybridise efficiently.

By "isolated" is meant material that is substantially or essentially free from components that normally accompany it in its native state. For example, an "isolated polynucleotide", as used herein, refers to a polynucleotide, which has been purified from the sequences which flank it in a naturally occurring state, e.g., a DNA fragment which has been removed from the sequences which are normally adjacent to the fragment.

By "marker gene" is meant a gene that imparts a distinct phenotype to cells expressing the marker gene and thus allows such transformed cells to be distinguished from cells that do not have the marker. A selectable marker gene confers a trait for which one can 'select' based on resistance to a selective agent (e.g., a herbicide, antibiotic, radiation, heat, or other treatment damaging to untransformed cells). A screenable marker gene (or reporter gene) confers a trait that one can identify through observation or testing, i.e., by 'screening' (e.g. β-glucuronidase, luciferase, or other enzyme activity not present in untransformed cells).

By "obtained from" is meant that a sample such as, for example, a nucleic acid extract is isolated from, or derived from, a particular source of the host. For example, the nucleic acid extract may be obtained from tissue isolated directly from the host.

The term "oligonucleotide" as used herein refers to a polymer composed of a multiplicity of nucleotide units (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotides and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule may vary depending on the particular application. An oligonucleotide is typically rather short in length, generally from about 10 to 30 nucleotides, but the term can refer to molecules of any length, although the term "polynucleotide" or "nucleic acid" is typically used for large oligonucleotides.

The term "operably connected" or "operably linked" as used herein means placing a structural gene under the regulatory control of a promoter, which then controls the transcription and optionally translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e. the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e. the genes from which it is derived.

As used herein, "plant" and "differentiated plant" refer to a whole plant or plant part containing differentiated plant cell types, tissues and/or organ systems. Plantlets and seeds are also included within the meaning of the foregoing terms. Plants included in the invention are any plants amenable to transformation techniques, including angiosperms, gymnosperms, monocotyledons and dicotyledons.

The term "plant cell" as used herein refers to any plant cell or cell line including protoplasts, gamete-producing cells, and cells which regenerate into whole plants. Plant cells also include cells in plants as well as protoplasts in culture.

By "plant tissue" is meant differentiated and undifferentiated tissue derived from roots, shoots, pollen, seeds, tumour tissue, such as crown galls, and various forms of aggregations of plant cells in culture, such as embryos and calluses.

The term "polynucleotide" or "nucleic acid" as used herein designates mRNA, RNA, cRNA, cDNA or DNA. The term typically refers to oligonucleotides greater than 30 nucleotides in length.

The terms "polynucleotide variant" and "variant" and the like refer to polynucleotides displaying substantial sequence identity with a reference polynucleotide sequence or polynucleotides that hybridise with a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. Accordingly, these terms encompass polynucleotides that initiate RNA transcription or that, when fused to a particular gene and introduced into a plant cell, cause expression of the gene at a level higher than is possible in the absence of such polynucleotides. The terms "polynucleotide variant" and "variant" also include naturally occurring allelic variants.

"Polypeptide", "peptide" and "protein" are used interchangeably herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers.

The term "polypeptide variant" refers to polypeptides that are distinguished from a reference polypeptide by the addition, deletion or substitution of at least one amino acid. In certain embodiments, a polypeptide variant is distinguished from a reference polypeptide by one or more substitutions, which may be conservative or non-conservative. In certain embodiments, the polypeptide variant comprises conservative substitutions and, in this regard, it is well understood in the art that some amino acids may be changed to others with broadly similar properties without changing the nature of the activity of the polypeptide. Polypeptide variants also encompass polypeptides in which one or more amino acids have been added or deleted, or replaced with different amino acid residues.

By "primer" is meant an oligonucleotide which, when paired with a strand of DNA, is capable of initiating the synthesis of a primer extension product in the presence of a suitable polymerising agent. The primer is typically single-stranded for maximum efficiency in amplification but may alternatively be double-stranded. A primer must be sufficiently long to prime the synthesis of extension products in the presence of the polymerisation agent. The length of the primer depends on many factors, including application, temperature to be employed, template reaction conditions, other reagents, and source of primers. For example, depending on the complexity of the target sequence, the oligonucleotide primer typically contains 15 to 35 or more nucleotides, although it may contain fewer nucleotides. Primers can be large polynucleotides, such as from about 200 nucleotides to several kilobases or more. Primers may be selected to be "substantially complementary" to the sequence on the template to which it is designed to hybridise and serve as a site for the initiation of synthesis. By "substantially complementary", it is meant that the primer is sufficiently complementary to hybridise with a target nucleotide sequence. Suitably, the primer contains no mismatches with the template to which it is designed to hybridise but this is not essential. For example, non-complementary nucleotides may be attached to the 5' end of the primer, with the remainder of the primer sequence being complementary to the template. Alternatively, non-complementary nucleotides or a stretch of non-complementary nucleotides can be interspersed into a primer, provided that the primer sequence has sufficient complementarity with the sequence of the template to hybridise therewith and thereby form a template for synthesis of the extension product of the primer.

"Probe" refers to a molecule that binds to a specific sequence or sub-sequence or other moiety of another molecule. Unless otherwise indicated, the term "probe" typically refers to a polynucleotide probe that binds to another nucleic acid, often called the "target nucleic acid", through complementary base pairing. Probes may bind target nucleic acids lacking complete sequence complementarity with the probe, depending on the stringency of the hybridisation conditions. Typically, probes comprise at least 15, 20, 30, 50, 100, 200, 400, 600, 1000 nucleotides. Probes can be labelled directly or indirectly.

The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably linked to the nucleotide sequence.

By "promoter" is meant a sequence of nucleotides from which transcription of DNA operably linked downstream of said sequence (i.e. in the 3' direction on the sense strand of double-stranded DNA) may be initiated.

By "recombinant polypeptide" is meant a polypeptide made using recombinant techniques, i.e., through the expression of a recombinant polynucleotide.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 50 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerised implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology", John. Wiley & Sons Inc, 1994-1998, Chapter 15.

The terms "sequence identity" and "identity" are used interchangeably herein to refer to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software.

The term "sequence similarity" and "similarity" are used interchangeably herein to refer to the percentage number of amino acids that are identical or constitute conservative substitutions as defined in the following table.

TABLE A

| Original Residue | Exemplary Substitutions | Preferred Substitutions |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Similarity may be determined using sequence comparison programs such as GAP (Deveraux et al. 1984, *Nucleic Acids Research* 12:387-395). In this way, sequences of a similar or substantially different length to those cited herein might be compared by insertion of gaps into the alignment, such gaps being determined, for example, by the comparison algorithm used by GAP.

"Stringency" as used herein, refers to the temperature and ionic strength conditions, and presence or absence of certain organic solvents, during hybridisation. The higher the stringency, the higher will be the degree of complementarity between immobilised nucleotide sequences and the labelled polynucleotide sequence.

"Stringent conditions" refers to temperature and ionic conditions under which only nucleotide sequences having a high frequency of complementary bases will hybridise. The stringency required is nucleotide sequence dependent and depends upon the various components present during hybridisation. Generally, stringent conditions are selected to be about 10 to 20° C. lower than the thermal melting point ($T_m$) for the specific sequence at a defined ionic strength and pH. The $T_m$ is the temperature (under defined ionic strength and pH) at which 50% of a target sequence hybridises to a complementary probe.

The term "transcribable DNA sequence" or "transcribed DNA sequence", excludes the non-transcribed regulatory sequence that drives transcription. Depending on the aspect of the invention, the transcribable sequence may be derived in whole or in part from any source known to the art, including a plant, a fungus, an animal, a bacterial genome or episome, eukaryotic, nuclear or plasmid DNA, cDNA, viral DNA or chemically synthesised DNA. A transcribable sequence may contain one or more modifications in either the coding or the untranslated regions, which could affect the biological activity or the chemical structure of the expression product, the rate of expression or the manner of expression control. Such modifications include, but are not limited to, insertions, deletions and substitutions of one or more nucleotides. The transcribable sequence may contain an uninterrupted coding sequence or it may include one or more introns, bound by the appropriate splice junctions. The transcribable sequence may also encode a fusion protein. It is contemplated that introduction into plant tissue of chimeric nucleic acid constructs of the invention will include constructions wherein the transcribable sequence and its promoter are each derived from different species.

The term "transformation" means alteration of the genotype of a host plant by the introduction of a chimeric nucleic acid.

The term "transgene" is used herein to describe genetic material that has been or is about to be artificially inserted into the genome of a cell, particularly a plant cell. The transgene is used to transform a cell, meaning that a permanent or transient genetic change, especially a permanent genetic change, is induced in a cell following incorporation of a chimeric DNA construct as defined herein. A permanent genetic change is generally achieved by introduction of the DNA into the genome of the cell.

As used herein, the term "transgenic" or "transformed" with respect to a plant cell, plant part (including seed), plant tissue or plant means a plant cell, plant part, plant tissue or plant which comprises an isolated chimeric DNA construct according to the invention which has been introduced into the nucleome, especially the genome, of a plant cell, plant part, plant tissue or plant.

By "transgenote" is meant an immediate product of a transformation process.

By "vector" is meant a nucleic acid molecule, suitably a DNA molecule derived, for example, from a plasmid, bacteriophage, or plant virus, into which a nucleic acid sequence may be inserted or cloned. A vector typically contains one or more unique restriction sites and may be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector may also include a selection marker such as an antibiotic resistance gene that can be used for selection of suitable transformants. Examples of such resistance genes are well known to those of skill in the art.

The terms "wild type", "native" or "non-transgenic" refers to an untransformed plant cell, plant part, plant tissue or plant, i.e. one where the nucleome, especially the genome, has not been altered by the presence of a chimeric DNA construct as defined herein.

2. Transcribed DNA Sequence

The promoter of the present invention was derived from a Papua New Guinea isolate of the badnavirus Taro Bacilliform virus (TaBV), which infects taro plants (*Colocasia esculenta*). The entire sequence of its circular genome, which is set forth in SEQ ID NO:2, extends 7458 nts and comprises three open reading frames (ORO. ORE 1 extends from position 350 through 790; ORE 2 extends from position 790 through 1224, and ORF 3 extends from position 1227 through 6872. For convenience, the nucleotide sequence corresponding to these open reading frames is presented in SEQ ID NO:1. An untranslated region (UTR) extends from nucleotide 6873 through nucleotide 349 of SEQ ID NO:2.

The open reading frames of the subject TaBV are highly transcribed in infected tissue of taro. Accordingly, nucleic acid sequences corresponding to these open reading frames may be useful as probes for isolating homologous sequences from other organisms including, but not limited to, viruses such as badnaviruses. These homologous sequences, in turn, permit the isolation of promoters from such other organisms, which have the same or similar constitutive qualities as the promoter sequences exemplified herein. Further, the homologous sequences and their encoded amino acid sequences are useful in diagnostic applications for detecting the presence of infecting virus particles in plants such as, for example, taro plants. Applications of this type include the use of detectable agents such as probes and antigen-binding molecules, which interact specifically with those sequences.

3. Polynucleotide Sequence Variants of Transcribed DNA Sequences

In general, homologous sequences or polynucleotide sequence variants of the invention comprise regions that show suitably at least 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence identity over a reference polynucleotide sequence of identical size ("comparison window") or when compared to an aligned sequence in which the alignment is performed by a computer homology program known in the art.

Polynucleotide sequence variants of the invention may be prepared according to the following procedure:
 (a) obtaining a nucleic acid extract from a suitable organism, which is preferably a virus, and more preferably a badnavirus;
 (b) creating primers which are optionally degenerate wherein each comprises a portion of a reference polynucleotide corresponding to a transcribable DNA sequence of the invention; and (c) using said primers to amplify, via nucleic acid amplification techniques, at least one amplification product from said nucleic acid extract, wherein said amplification product corresponds to a polynucleotide sequence variant.

Suitable nucleic acid amplification techniques are well known to the skilled addressee, and include polymerase chain reaction (PCR) as for example described in Ausubel et al. (supra); strand displacement amplification (SDA) as for example described in U.S. Pat. No 5,422,252; rolling circle replication (RCR) as for example described in Liu et al., (1996, *J. Am. Chem. Soc.* 118:1587-1594 and International application WO 92/01813) and Lizardi et al., (International Application WO 97/19193) nucleic acid sequence-based amplification (NASBA) as for example described by Sooknanan et al., (1994, *Biotechniques* 17:1077-1080); and Q-β replicase amplification as for example described by Tyagi et al., (1996, *Proc. Natl. Acad. Sci. USA* 93:5395-5400).

Typically, polynucleotide sequence variants that are substantially complementary to a reference polynucleotide are identified by blotting techniques that include a step whereby nucleic acids are immobilised on a matrix (preferably a synthetic membrane such as nitrocellulose), followed by a hybridisation step, and a detection step. Southern blotting is used to identify a complementary DNA sequence; northern blotting is used to identify a complementary RNA sequence. Dot blotting and slot blotting can be used to identify complementary DNA/DNA, DNA/RNA or RNA/RNA polynucleotide sequences. Such techniques are well known by those skilled in the art, and have been described in Ausubel et al. (1994-1998, supra) at pages 2.9.1 through 2.9.20.

According to such methods, Southern blotting involves separating DNA molecules according to size by gel electrophoresis, transferring the size-separated DNA to a synthetic membrane, and hybridising the membrane-bound DNA to a complementary nucleotide sequence labelled radioactively, enzymatically or fluorochromatically. In dot blotting and slot blotting, DNA samples are directly applied to a synthetic membrane prior to hybridisation as above.

An alternative blotting step is used when identifying complementary polynucleotides in a cDNA or genomic DNA library, such as through the process of plaque or colony hybridisation. A typical example of this procedure is described in Sambrook et al. ("Molecular Cloning. A Laboratory Manual", Cold Spring Harbour Press, 1989) Chapters 8-12.

Typically, the following general procedure can be used to determine hybridisation conditions. Polynucleotides are blotted/transferred to a synthetic membrane, as described above. A reference polynucleotide such as a polynucleotide of the invention is labelled as described above, and the ability of this labelled polynucleotide to hybridise with an immobilised polynucleotide is analysed.

A skilled addressee will recognise that a number of factors influence hybridisation. The specific activity of radioactively labelled polynucleotide sequence should typically be greater than or equal to about $10^8$ dpm/mg to provide a detectable signal. A radiolabelled nucleotide sequence of specific activity $10^8$ to $10^9$ dpm/mg can detect approximately 0.5 pg of DNA. It is well known in the art that sufficient DNA must be immobilised on the membrane to permit detection. It is desirable to have excess immobilised DNA, usually 10 μg. Adding an inert polymer such as 10% (w/v) dextran sulphate (MW 500,000) or polyethylene glycol 6000 during hybridisation can also increase the sensitivity of hybridisation (see Ausubel supra at 2.10.10).

To achieve meaningful results from hybridisation between a polynucleotide immobilised on a membrane and a labelled polynucleotide, a sufficient amount of the labelled polynucleotide must be hybridised to the immobilized polynucleotide following washing. Washing ensures that the labelled polynucleotide is hybridised only to the immobilized polynucleotide with a desired degree of complementarity to the labelled polynucleotide.

It will be understood that polynucleotide variants according to the invention will hybridise to a reference polynucleotide under at least low stringency conditions. Reference herein to low stringency conditions include and encompass from at least about 1% v/v to at least about 15% v/v formamide and from at least about 1 M to at least about 2 M salt for hybridisation at 42° C., and at least about 1 M to at least about 2 M salt for washing at 42° C. Low stringency conditions also may include 1% Bovine Serum Albumin (BSA), 1 mM EDTA, 0.5 M $NaHPO_4$ (pH 7.2), 7% SDS for hybridisation at 65° C., and (i) 2×SSC, 0.1% SDS; or (ii) 0.5% BSA, 1 mM EDTA, 40 mM $NaHPO_4$ (pH 7.2), 5% SDS for washing at room temperature.

Suitably, the polynucleotide variants hybridise to a reference polynucleotide under at least medium stringency conditions, Medium stringency conditions include and encompass from at least about 16% v/v to at least about 30% v/v formamide and from at least about 0.5 M to at least about 0.9 M salt for hybridisation at 42° C., and at least about 0.5 M to at least about 0.9 M salt for washing at 42° C. Medium stringency conditions also may include 1% Bovine Serum. Albumin (BSA), 1 mM EDTA, 0.5 M $NaHPO_4$ (pH 7.2), 7% SDS for hybridisation at 65° C., and (i) 2×SSC, 0.1% SDS; or (ii) 0.5% BSA, 1 mM EDTA, 40 mM. $NaHPO_4$ (pH 7.2), 5% SDS for washing at 42° C.

Desirably, the polynucleotide variants hybridise to a reference polynucleotide under high stringency conditions High stringency conditions include and encompass from at least about 31% v/v to at least about 50% v/v formamide and from at least about 0.01 M to at least about 0.15 M salt for hybridisation at 42° C., and at least about 0.01 M to at least about 0.15 M salt for washing at 42° C. High stringency conditions also may include 1% BSA, 1 mM EDTA, 0.5 M $NaHPO_4$ (pH 7.2), 7% SDS for hybridisation at 65° C., and (i) 0.2×SSC, 0.1% SDS; or (ii) 0.5% BSA, 1 mM EDTA, 40 mM $NaHPO_4$ (pH 7.2), 1% SDS for washing at a temperature in excess of 65° C.

Other stringent conditions are well known in the art. A skilled addressee will recognise that various factors can be manipulated to optimise the specificity of the hybridisation. Optimisation of the stringency of the final washes can serve to ensure a high degree of hybridisation. For detailed examples, see Ausubel et al., supra at pages 2.10.1 to 2.10.16 and Sambrook et al. (1989, supra) at sections 1.101 to 1.104.

While stringent washes are typically carried out at temperatures from about 42° C. to 68° C., one skilled in the art will appreciate that other temperatures may be suitable for stringent conditions. Maximum hybridisation typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel et al., supra at page 2.10.8).

In general, washing is carried out at $T=69.3+0.41$ (G+C)% -12° C. However, the $T_m$ of a duplex DNA decreases by 1° C. with every increase of 1% in the number of mismatched base pairs.

In an exemplary hybridisation procedure, a membrane (e.g., a nitrocellulose membrane or a nylon membrane) containing immobilised DNA is hybridised overnight at 42° C. in a hybridisation buffer (50% deionised formamide, 5×SSC, 5×Denhardt's solution (0.1% ficoll, 0.1% polyvinylpyrollidone and 0.1% bovine serum albumin), 0.1% SDS and 200 mg/mL denatured salmon sperm DNA) containing labelled probe. The membrane is then subjected to two sequential medium stringency washes (i.e., 2×SSC/0.1% SDS for 15 min at 45° C., followed by 2×SSC/0.1% SDS for 15 min at 50° C.), followed by two sequential high stringency washes (i.e., 0.2×SSC/0.1% SDS for 12 min. at 55° C. followed by 0.2×SSC and 0.1% SDS solution for 12 min).

Methods for detecting a labelled polynucleotide hybridised to an immobilised polynucleotide are well known to practitioners in the art. Such methods include autoradiography, phosphorimaging, and chemiluminescent, fluorescent and colorimetric detection.

4. Polypeptides Encoded by the Transcribed DNA Sequence

The TaBV genomic sequence comprises three ORFs, which encode the amino acid sequences set forth in SEQ ID NO:3, 4 and 5, respectively. Sequence comparisons between these ORFs and the ORFs of other badnaviruses including those of BSV, ComYMV, CSSV, CYMV, DaBV and SCBV, showed sequences identities ranging from 20-37% for ORF 1, 13-23% for ORF 2 and 30-37% for ORF 3. ORF 3 showed most similarity to that of other badnaviruses due to the presence of conserved motifs common to other badnaviruses including movement motifs, the RNA-binding domain (RB; C-X2-C-X4-H-X4-C) (SEQ ID NO:30), the second cysteine rich sequence (CYS) of unknown function, the aspartic protease motifs, reverse transcriptase domains and RNase H domains.

The amino acid sequences corresponding to these ORFs or portions thereof, are useful inter alia as targets in diagnostic applications for detecting badnavirus infections, especially TaBV infections and as immunogens for the preparation of antigen-binding molecules that are interactive with amino acid sequences encoded by those ORFs. Useful portions, which are contemplated by the present invention, are at least 6, 7, 8, 9, 10, 11, 12, 13, 14, 15, 16, 17, 18, 19, 20, 21, 22, 23, 24, 25, 26, 27, 28, 29, 30 amino acid residues in length.

5. Polypeptide Variants

The invention also contemplates polypeptide variants of the polypeptides encoded by the TaBV ORFs described above. In general, these polypeptide variants will comprise regions that show preferably at least 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence similarity to any one of the sequences set forth in SEQ ID NO:3, 4 and 5. It is preferred that variants display at least 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence identity to the sequence set forth in any one of SEQ ID NO:3, 4 or 5.

6. Promoter Sequences of the Invention 6.1 Promoter Region of Transcribed DNA Sequence The invention also provides an isolated promoter, located in the UTR between the end of ORF 3 and the start of ORF 1, which extends to include a tRNA$^{met}$-binding site at positions 1-12. In particular, an isolated polynucleotide comprising a constitutive promoter sequence for expression of chimeric or heterologous genes in plants, especially monocotyledonous plants, is provided and is set forth in SEQ ID NO:6. This promoter sequence is also referred to hereinafter as the TaBV promoter.

The invention also contemplates biologically active portions of SEQ ID NO:6 representative examples of which include the polynucleotide set forth in any one of SEQ ID NO:7, 8 and 9 as well as polynucleotide sequence variants thereof. Those of skill in the art will understand that a biologically active portion or fragment of a promoter sequence, when fused to a particular gene and introduced into a plant cell, causes expression of the gene at a level higher than is possible in the absence of such fragment. One or more biologically active fragments may be included in a promoter according to the present invention, for instance one or more motifs may be coupled to a "minimal" promoter. Such motifs may confer TaBV promoter function on a promoter, such as suitability for enhanced performance in monocotyledonous plants and especially in non-graminaceous monocotyledonous plants such as, but not limited to, Musaceae (*Musa* and *Ensete*), taro, ginger, onions, garlic, pineapple, bromeliaeds, palms, orchids, lilies, irises and the like.

The activity of a promoter can be determined by methods well known in the art. For example, the level of promoter activity is quantifiable by assessment of the amount of mRNA produced by transcription from the promoter or by assessment of the amount of protein product produced by translation of mRNA produced by transcription from the promoter. The amount of a specific mRNA present in an expression system may be determined for example using specific oligonucleotides which are able to hybridise with the mRNA and which are labelled or may be used in a specific amplification reaction such as PCR. Use of a reporter gene facilitates determination of promoter activity by reference to protein production. Non-limiting methods for assessing promoter activity are disclosed by Medberry et al. (1992, *Plant Cell* 4:185; 1993, *The Plant J.* 3:619), Sambrook et al. (1989, supra) and McPherson et al, (U.S. Pat. No. 5,164,316).

6.2 Promoter Variants

Promoter variants that are substantially complementary to a reference promoter of the invention may be obtained by procedures outlined in Section 3. In general, these promoter variants will comprise regions that show identity values as described in Section 3. What constitutes suitable variants may be determined by conventional techniques. For example, polynucleotides according to SEQ ID NO:6, 7, 8 and 9 can be mutated using random mutagenesis (e.g., transposon mutagenesis), oligonucleotide-mediated (or site-directed) mutagenesis, PCR mutagenesis and cassette mutagenesis of an earlier prepared variant or non-variant version of an isolated natural promoter according to the invention.

Oligonucleotide-mediated mutagenesis is a preferred method for preparing nucleotide substitution variants of a promoter of the invention. This technique is well known in the art as, for example, described by Adelman et al. (1983, *DNA* 2:183). Briefly, promoter DNA is altered by hybridising an oligonucleotide encoding the desired mutation to a template DNA, where the template is the single-stranded form of a plasmid or bacteriophage containing the unaltered or native DNA sequence of the promoter of interest. After hybridisation, a DNA polymerase is used to synthesise an entire second complementary strand of the template that will thus incorporate the oligonucleotide primer, and will code for the selected alteration in the promoter of interest.

Generally, oligonucleotides of at least 20 nucleotides in length are used. An optimal oligonucleotide will have 12 to 15 nucleotides that are completely complementary to the template on either side of the nucleotide(s) coding for the mutation. This ensures that the oligonucleotide will hybridise properly to the single-stranded DNA template molecule.

The DNA template can be generated by those vectors that are either derived from bacteriophage M13 vectors, or those vectors that contain a single-stranded phage origin of replication as described by Viera et al. (1987, *Methods Enzymol.* 153:3). Thus, the DNA that is to be mutated may be inserted into one of the vectors to generate single-stranded template. Production of single-stranded template is described, for example, in Sections 4.21-4.41 of Sambrook et al. (1989, supra).

Alternatively, the single-stranded template may be generated by denaturing double-stranded plasmid (or other DNA) using standard techniques.

For alteration of the native DNA sequence, the oligonucleotide is hybridised to the single-stranded template under suitable hybridisation conditions. A DNA polymerising enzyme, usually the Klenow fragment of DNA polymerase 1, is then added to synthesise the complementary strand of the template using the oligonucleotide as a primer for synthesis. A heteroduplex molecule is thus formed such that one strand of DNA encodes the mutated form of the promoter under test, and the other strand (the original template) encodes the native unaltered sequence of the promoter under test. This heteroduplex molecule is then transformed into a suitable host cell, usually a prokaryote such as *E. coli*. After the cells are grown, they are plated onto agarose plates and screened using the oligonucleotide primer having a detectable label to identify the bacterial colonies having the mutated DNA. The resultant mutated DNA fragments are then cloned into suitable expression hosts such as *E. coli* using conventional technology and clones that retain the desired promoter activity are detected. Where the clones have been derived using random mutagenesis techniques, positive clones would have to be sequenced in order to detect the mutation.

Alternatively, linker-scanning mutagenesis of DNA may be used to introduce clusters of point mutations throughout a sequence of interest that has been cloned into a plasmid vector. For example, reference may be made to Ausubel et al., supra, (in particular, Chapter 8.4) which describes a first protocol that uses complementary oligonucleotides and requires a unique restriction site adjacent to the region that is to be mutagenised. A nested series of deletion mutations is first generated in the region. A pair of complementary oligonucleotides is synthesised to fill in the gap in the sequence of interest between the linker at the deletion endpoint and the nearby restriction site. The linker sequence actually provides the desired clusters of point mutations as it is moved or "scanned" across the region by its position at the varied endpoints of the deletion mutation series. An alternate protocol is also described by Ausubel et al., supra, which makes use of site directed mutagenesis procedures to introduce small clusters of point mutations throughout the target region. Briefly, mutations are introduced into a sequence by annealing a synthetic oligonucleotide containing one or more mismatches to the sequence of interest cloned into a single-stranded M13 vector. This template is grown in an *Escherichia coli* dut⁻ ung⁻ strain, which allows the incorporation of uracil into the template strand. The oligonucleotide is annealed to the template and extended with T4 DNA polymerase to create a double-stranded heteroduplex. Finally, the heteroduplex is introduced into a wild-type *E. coli* strain, which will prevent replication of the template strand due to the presence of apurinic sites (generated where uracil is incorporated), thereby resulting in plaques containing only mutated DNA.

Region-specific mutagenesis and directed mutagenesis using PCR may also be employed to construct promoter variants according to the invention. In this regard, reference may be made, for example, to Ausubel et al., supra, in particular Chapters 8.2A and 8.5.

7. Chimeric DNA Construct

A promoter or biologically active variant or fragment according to the invention can be fused to a foreign or endogenous DNA sequence to create a chimeric DNA construct for introduction into plants.

7.1 3' Non-translated Region

In some embodiments, the chimeric DNA construct of the present invention is in the form of an expression cassette designed for genetic transformation of plants. In this embodiment, the chimeric DNA construct suitably comprises a 3' non-translated sequence that is operably linked to the foreign or endogenous DNA sequence and that functions in plant cells to terminate transcription and/or to cause addition of a polyadenylated nucleotide sequence to the 3' end of a RNA sequence transcribed from the foreign or endogenous DNA sequence. Thus, a 3' non-translated sequence refers to that portion of a gene comprising a DNA segment that contains a transcriptional termination signal and/or a polyadenylation signal and any other regulatory signals (e.g., translational termination signals) capable of effecting mRNA processing or gene expression. The polyadenylation signal is characterised by effecting the addition of polyadenylic acid tracts to the 3' end of the mRNA precursor. Polyadenylation signals are commonly recognised by the presence of homology to the canonical form 5' AATAAA-3' although variations are not uncommon.

The 3' non-translated regulatory DNA sequence preferably includes from about 50 to 1,000 nucleotide base pairs and contains plant transcriptional and translational termination sequences. Examples of suitable 3' non-translated sequences are the 3' transcribed non-translated regions containing a polyadenylation signal from the nopaline synthase (nos) gene of *Agrobacterium tumefaciens* (Bevan et al., 1983, *Nucl. Acid Res.*, 11:369) and the terminator for the T7 transcript from the octopine synthase gene of *Agrobacterium tumefaciens*. Alternatively, suitable 3' non-translated sequences may be derived from plant genes such as the 3' end of the protease inhibitor I or II genes from potato or tomato, the soybean storage protein genes and the pea E9 small subunit of the ribulose-1,5-bisphosphate carboxylase (ssRUBISCO) gene, although other 3' elements known to those of skill in the art can also be employed. Alternatively, 3' non-translated regulatory sequences can be obtained de novo as, for example, described by An (1987, *Methods in Enzymology,* 153:292).

7.2 Optional Sequences

The chimeric DNA construct of the present invention can further include enhancers, either translation or transcription enhancers, as may be required. These enhancer elements are well known to persons skilled in the art, and can include the ATG initiation codon and adjacent sequences. The initiation codon must be in phase with the reading frame of the coding sequence relating to the foreign or endogenous DNA sequence to ensure translation of the entire sequence. The translation control signals and initiation codons can be of a variety of origins, both natural and synthetic. Translational initiation regions may be provided from the source of the transcriptional initiation region, or from the foreign or endogenous DNA sequence. The sequence can also be derived from the source of the promoter selected to drive transcription, and can be specifically modified so as to increase translation of the mRNA.

Examples of transcriptional enhancers include, but are not restricted to, elements from the CaMV 35S promoter and octopine synthase genes as for example described by Last et al. (U.S. Pat. No. 5,290,924). It is proposed that the use of an enhancer element such as the ocs element, and particularly multiple copies of the element, will act to increase the level of transcription from adjacent promoters when applied in the context of plant transformation. As the DNA sequence inserted between the transcription initiation site and the start of the coding sequence, i.e., the untranslated leader sequence, can influence gene expression, one can also employ a particular leader sequence. Preferred leader sequences include those that comprise sequences selected to direct optimum expression of the foreign or endogenous DNA sequence. For example, such leader sequences include a preferred consensus sequence which can increase or maintain mRNA stability and prevent inappropriate initiation of translation as for example described by Joshi (1987, *Nucl. Acid Res.*, 15:6643). However, other leader sequences, e.g., the leader sequence of RTBV, have a high degree of secondary structure that is expected to decrease mRNA stability and/or decrease translation of the mRNA. Thus, leader sequences (i) that do not have a high degree of secondary structure, (ii) that have a high degree of secondary structure where the secondary structure does not inhibit mRNA stability and/or decrease translation, or (iii) that are derived from genes that are highly expressed in plants, will be most preferred.

Regulatory elements such as the sucrose synthase intron as, for example, described by Vasil et al. (1989, Plant Physiol., 91:5175), the Adh intron I as, for example, described by Callis et al. (1987, *Genes Develop., II*), or the TMV omega element as, for example, described by Gallie et al, (1989, *The Plant Cell,* 1:301) can also be included where desired. Other such regulatory elements useful in the practice of the invention are known to those of skill in the art.

Additionally, targeting sequences may be employed to target a protein product of the foreign or endogenous DNA sequence to an intracellular compartment within plant cells or to the extracellular environment. For example, a DNA sequence encoding a transit or signal peptide sequence may be operably linked to a sequence encoding a desired protein such that, when translated, the transit or signal peptide can transport the protein to a particular intracellular or extracellular destination, respectively, and can then be post-translationally removed. Transit or signal peptides act by facilitating the transport of proteins through intracellular membranes, e.g., vacuole, vesicle, plastid and mitochondrial membranes, whereas signal peptides direct proteins through the extracellular membrane. For example, the transit or signal peptide can direct a desired protein to a particular organelle such as a plastid (e.g., a chloroplast), rather than to the cytoplasm. Thus, the chimeric DNA construct can further comprise a plastid transit peptide encoding DNA sequence operably linked between a promoter or biologically active variant or fragment according to the invention and the foreign or endogenous DNA sequence. For example, reference may be made to Heijne et al. (1989, *Eur. J. Biochem.*, 180:535) and Keegstra et al. (1989, *Ann. Rev. Plant Physiol. Plant Mol. Biol.*, 40:471).

A chimeric DNA construct can also be introduced into a vector, such as a plasmid. Plasmid vectors include additional DNA sequences that provide for easy selection, amplification, and transformation of the expression cassette in prokaryotic and eukaryotic cells, e.g., pUC-derived vectors, pSK-derived vectors, pGEM-derived vectors, pSP-derived vectors, or pBS-derived vectors. Additional DNA sequences include origins of replication to provide for autonomous replication of the vector, selectable marker genes, preferably encoding antibiotic or herbicide resistance, unique multiple cloning sites providing for multiple sites to insert DNA sequences or genes encoded in the chimeric DNA construct, and sequences that enhance transformation of prokaryotic and eukaryotic cells.

The vector suitably contains an element(s) that permits stable integration of the vector into the host cell genome or autonomous replication of the vector in the cell independent of the genome of the cell. The vector may be integrated into the host cell genome when introduced into a host cell. For integration, the vector may rely on the foreign or endogenous DNA sequence or any other element of the vector for stable integration of the vector into the genome by homologous recombination. Alternatively, the vector may contain additional nucleic acid sequences for directing integration by homologous recombination into the genome of the host cell. The additional nucleic acid sequences enable the vector to be integrated into the host cell genome at a precise location in the chromosome. To increase the likelihood of integration at a precise location, the integrational elements should desirably contain a sufficient number of nucleic acids, such as 100 to 1,500 base pairs, usually 400 to 1,500 base pairs, and more usually 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAM.beta.1 permitting replication in *Bacillus*. The origin of replication may be one having a mutation to make its function temperature-sensitive in a *Bacillus* cell (see, e.g., Ehrlich, 1978, *Proc. Natl. Acad. Sci. USA* 75:1433).

7.3 Marker Genes

To facilitate identification of transformants, the chimeric DNA construct desirably comprises a selectable or screenable marker gene as, or in addition to, the expressible foreign or endogenous DNA sequence. The actual choice of a marker is not crucial as long as it is functional in combination with the plant cells of choice. The marker gene and the foreign or endogenous DNA sequence of interest do not have to be linked, since co-transformation of unlinked genes as, for example, described in U.S. Pat. No. 4,399,216 is also an efficient process in plant transformation.

Included within the terms selectable or screenable marker genes are genes that encode a "secretable marker" whose secretion can be detected as a means of identifying or selecting for transformed cells. Examples include markers that encode a secretable antigen that can be identified by antibody interaction, or secretable enzymes that can be detected by their catalytic activity. Secretable proteins include, but are not restricted to, proteins that are inserted or trapped in the cell wall (e.g., proteins that include a leader sequence such as that found in the expression unit of extensin or tobacco PR-S); small, diffusible proteins detectable, e.g. by ELISA; and small active enzymes detectable in extracellular solution (e.g., α-amylase, β-lactamase, phosphinothricin acetyltransferase).

7.4 Selectable Markers

Examples of bacterial selectable markers are the dal genes from *Bacillus subtilis* or *Bacillus licheniformis*, or markers that confer antibiotic resistance such as ampicillin, kanamycin, erythromycin, chloramphenicol or tetracycline resistance. Exemplary selectable markers for selection of plant transformants include, but are not limited to, a hyg gene which encodes hygromycin B resistance; a neomycin phosphotransferase (neo) gene conferring resistance to kanamycin, paromomycin, G418 and the like as, for example, described by Potrykus et al. (1985, *Mol. Gen. Genet.* 199: 183); a glutathione-S-transferase gene from rat liver conferring resistance to glutathione derived herbicides as, for example, described in EP-A 256 223; a glutamine synthetase gene conferring, upon overexpression, resistance to glutamine synthetase inhibitors such as phosphinothricin as, for example, described WO87/05327, an acetyl transferase gene from *Streptomyces viridochromogenes* conferring resistance to the selective agent phosphinothricin as, for example, described in EP-A 275 957, a gene encoding a 5-enolshikimate-3-phosphate synthase (EPSPS) conferring tolerance to N-phosphonomethylglycine as, for example, described by Hinchee et al. (1988, *Biotech.,* 6:915), a bar gene conferring resistance against bialaphos as, for example, described in WO91/02071; a nitrilase gene such as bxn from *Klebsiella ozaenae* which confers resistance to bromoxynil (Stalker et al., 1988, *Science,* 242:419); a dihydrofolate reductase (DHFR) gene conferring resistance to methotrexate (Thillet et al., 1988, *J. Biol. Chem.,* 263:12500); a mutant acetolactate synthase gene (ALS), which confers resistance to imidazolinone, sulfonylurea or other ALS-inhibiting chemicals (EP-A-154 204); a mutated anthranilate synthase gene that confers resistance to 5-methyl tryptophan; or a dalapon dehalogenase gene that confers resistance to the herbicide.

7.5 Screenable Markers

Preferred screenable markers include, but are not limited to, a uidA gene encoding a β-glucuronidase (GUS) enzyme for which various chromogenic substrates are known; a β-galactosidase gene encoding an enzyme for which chromogenic substrates are known; an aequorin gene (Prasher et al., 1985, *Biochem. Biophys. Res. Comm.,* 126:1259), which may be employed in calcium-sensitive bioluminescence detection; a green fluorescent protein gene (Niedz et al., 1995 *Plant Cell Reports,* 14:403); a luciferase (luc) gene (Ow et al., 1986. *Science,* 234:856), which allows for bioluminescence detection; a β-lactamase gene (Sutcliffe, 1978, *Proc. Natl. Acad. Sci. USA* 75:3737), which encodes an enzyme for which various chromogenic substrates are known (e.g., PADAC, a chromogenic cephalosporin); an R-locus gene, encoding a product that regulates the production of anthocyanin pigments (red colour) in plant tissues (Dellaporta et al., 1988, in *Chromosome Structure and Function,* pp. 263-282); an α-amylase gene Malta et al., 1990, *Biotech.,* 8:241); a tyrosinase gene (Katz et al., 1983, *J. Gen. Microbiol.,* 129:2703) which encodes an enzyme capable of oxidizing tyrosine to dopa and dopaquinone which in turn condenses to form the easily detectable compound melanin; or a xylE gene (Zukowsky et al., 1983, *Proc. Natl. Acad. Sci. USA* 80:1101), which encodes a catechol dioxygenase that can convert chromogenic catechols.

8. Uses of the Promoter of the Invention

The isolated promoter sequence may be used, inter alia, to drive expression of a foreign or endogenous DNA sequence. The foreign or endogenous DNA sequence may comprise a region transcribed into an RNA molecule that modulates the expression of a corresponding target gene. Such modulation of expression may be achieved, for example, by antisense technology, ribozyme technology and co-suppression or homology-dependent gene silencing, as is known in the art. Accordingly, the transcript may comprise an antisense RNA molecule, or a ribozyme or other transcript (such as inverted repeats and dsRNA, as mentioned, for instance, below) aimed at downregulation of expression of the corresponding target gene.

Thus, in some embodiments, the transcript is an antisense RNA molecule that directly blocks the translation of mRNA transcribed from a target gene by binding to the mRNA and preventing protein translation. When employed, antisense RNAs should be at least about 10-20 nucleotides or greater in length, and be at least about 75% complementary to their target genes or gene transcripts such that expression of the targeted homologous sequence is precluded.

In other embodiments, the transcript is a ribozyme that functions to inhibit the translation of a target gene mRNA. Ribozymes are enzymatic RNA molecules capable of catalysing the specific cleavage of RNA. The mechanism of ribozyme action involves sequence specific hybridisation of the ribozyme molecule to complementary target RNA, followed by an endonucleolytic cleavage. Within the scope of the invention are engineered hammerhead motif ribozyme molecules that specifically and efficiently catalyse endonucleolytic cleavage of target gene RNA sequences. Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. When employed, ribozymes may be selected from the group consisting of hammerhead ribozymes, axehead ribozymes, newt satellite ribozymes, Tetrahymena ribozymes and RNAse P, and are designed according to methods known in the art based on the sequence of the target gene (for instance, see U.S. Pat. No. 5,741,679). The suitability of candidate targets may also be evaluated by testing their accessibility to hybridisation with complementary oligonucleotides, using ribonuclease protection assays.

In other embodiments, the transcript is an RNA molecule that mediates RNA interference (RNAi) of a target gene or gene transcript. RNAi refers to interference with or destruction of the product of a target gene by introducing a single stranded, and typically a double stranded RNA (dsRNA), which is homologous to the transcript of a target gene. Thus, in some embodiments, dsRNA per se and especially dsRNA-producing constructs corresponding to at least a portion of a target gene may be used to decrease its level and/or functional activity. RNAi-mediated inhibition of gene expression may be accomplished using any of the techniques reported in the art, for instance by transfecting a nucleic acid construct encoding a stem-loop or hairpin RNA structure into the genome of the target cell, or by expressing a transfected nucleic acid construct having homology for a target gene from between convergent promoters, or as a head to head or tail to tail duplication from behind a single promoter. Any similar construct may be used so long as it produces a single RNA having the ability to fold back on itself and produce a dsRNA, or so long as it produces two separate RNA transcripts which then anneal to form a dsRNA having homology to a target gene.

Absolute homology is not required for RNAi, with a lower threshold being described at about 85% homology for a dsRNA of about 200 base pairs (Plasterk and Ketting, 2000, *Current Opinion in Genetics and Dev.* 10: 562-67). Therefore, depending on the length of the dsRNA, the RNAi-encoding nucleic acids can vary in the level of homology they contain toward the target gene transcript, i.e., with dsRNAs of 100 to 200 base pairs having at least about 85% homology with the target gene, and longer dsRNAs, i.e., 300 to 100 base pairs, having at least about 75% homology to the target gene. RNA-encoding constructs that express a single RNA transcript designed to anneal to a separately expressed RNA, or single constructs expressing separate transcripts from convergent promoters, are preferably at least about 100 nucleotides in length. RNA-encoding constructs that express a single RNA designed to form a dsRNA via internal folding are preferably at least about 200 nucleotides in length.

The promoter used to express the dsRNA-forming construct may be any type of promoter if the resulting dsRNA is specific for a gene product in the cell lineage targeted for destruction. Alternatively, the promoter may be lineage specific in that it is only expressed in cells of a particular development lineage. This might be advantageous where some overlap in homology is observed with a gene that is expressed in a non-targeted cell lineage. The promoter may also be inducible by externally controlled factors, or by intracellular environmental factors.

In another embodiment, RNA molecules of about 21 to about 23 nucleotides, which direct cleavage of specific mRNA to which they correspond, as for example described by Tuschl et al. in U.S. Patent Application No, 20020086356, can be utilised for mediating RNAi. Such 21-23 nt RNA molecules can comprise a 3' hydroxyl group, can be single-stranded or double stranded (as two 21-23 nt RNAs) wherein the dsRNA molecules can be blunt ended or comprise overhanging ends (e.g., 5', 3').

In other embodiments, the foreign or endogenous DNA sequence encodes: a detectable or measurable product, e.g. β-glucuronidase or luciferase; a selectable product, e.g., neomycin phosphotransferase (nptII) conferring resistance to aminoglycosidic antibiotics such as geneticin and paromomycin; a product conferring herbicide tolerance, e.g. glyphosate resistance or glufosinate resistance; a product affecting starch biosynthesis or modification e.g. starch branching enzyme, starch synthases, ADP-glucose pyrophosphorylase; a product involved in fatty acid biosynthesis, e.g. desaturase or hydroxylase; a product conferring insect resistance, e.g. crystal toxin protein of *Bacillus thuringiensis*; a product conferring viral resistance, e.g. viral coat protein; a product conferring fungal resistance, c.a. chitinase, β-1,3-glucanase or phytoalexins; a product altering sucrose metabolism, c.a. invertase or sucrose synthase; a gene encoding valuable pharmaceuticals, e.g. antibiotics, secondary metabolites, pharmaceutical peptides or vaccines.

The foreign or endogenous DNA sequence includes, but is not limited to, DNA from plant genes, and non-plant genes such as those from bacteria, yeasts, animals or viruses. Moreover, it is within the scope of the invention to isolate a foreign or endogenous DNA sequence from a given plant genotype, and to subsequently introduce multiple copies of that sequence into the same genotype, e.g., to enhance production of a given gene product. The introduced DNA can include modified genes, portions of genes, or chimeric genes, including genes from the same or different plant genotype.

Exemplary agronomic properties encoded by the foreign or endogenous DNA sequence include, but are not limited to: traits that are beneficial to the grower such as resistance to water deficit, pest resistance or tolerance, herbicide resistance or tolerance, disease resistance or tolerance (e.g., resistance to viruses or fungal pathogens), stress tolerance (increased salt tolerance) and improved food content or increased yields; traits that are beneficial to the consumer of the horticultural produce harvested from the plant such as improved nutritive content in human food or animal feed; or beneficial to the food processor such as improved processing traits. In such uses, the transgenic plants containing the promoter of the invention are generally grown for the use of their grain, fruit and other plant parts, including stalks, husks, vegetative parts, and the like in human or animal foods including use as part of animal silage or for ornamental purposes. Often, chemical constituents of crops are extracted for foods or industrial use and transgenic plants may be created which have enhanced or modified levels of such components.

The isolated promoter sequence of the invention may also find use in the commercial manufacture of proteins or other compounds, where the compound of interest is extracted or purified from plant parts, seeds, and the like. Such proteins or compounds include, but are not limited to, immunogenic molecules for use in vaccines, cytokines and hormones. Cells or tissue from the plants may also be cultured, grown in vitro, or fermented to manufacture such molecules.

The transgenic plants containing the isolated promoter sequence of the invention may also be used in commercial breeding programs, or may be crossed or bred to plants of related crop species. Improvements encoded by the foreign or endogenous DNA sequence may be transferred, e.g., from cells of one plant species to cells of another plant species, e.g., by protoplast fusion.

The transgenic plants containing the isolated promoter sequence of the invention may have many uses in research or breeding, including creation of new mutant plants through insertional mutagenesis, in order to identify beneficial mutants that might later be created by traditional mutation and selection. An example would be the introduction of a recombinant DNA sequence encoding a transposable element that may be used for generating genetic variation or the introduction of unique "signature sequences" or other marker sequences which can be used to identify proprietary lines or varieties.

9. Introduction of Chimeric Construct Into Plant Cells

Generally, the present invention employs recipient plant cells that are susceptible to transformation and subsequent regeneration into stably transformed, fertile plants. For monocot transformation for example, immature embryos, meristematic tissue, gametic tissue, embryogenic suspension cultures or embryogenic callus tissue can be employed as a source of recipient cells which is useful in the practice of the invention. For dicot transformation, organ and tissue cultures can be employed as a source of recipient cells. Thus, tissues, e.g., leaves, seed and roots, of divots can provide a source of recipient cells useful in the practice of the invention.

Cultured susceptible recipient cells are preferably grown on solid supports. Nutrients are provided to the cultures in the form of media and the environmental conditions for the cultures are controlled. Media and environmental conditions which support the growth of regenerable plant cultures are well known to the art.

A number of techniques are available for the introduction of DNA into a recipient plant cell. There are many plant transformation techniques well known to workers in the art, and new techniques are continually becoming known. The particular choice of a transformation technology will be determined by its efficiency to transform certain plant species as well as the experience and preference of the person practising the invention with a particular methodology of choice. It will be apparent to the skilled person that the particular choice of a transformation system to introduce a chimeric DNA construct into plant cells is not essential to or a limitation of the invention, provided it achieves an acceptable level of nucleic acid transfer. Guidance in the practical implementation of transformation systems for plant improvement is provided, for example, by Birch (1997, Annu. Rev. Plant Physiol. Plant Molec. Biol. 48: 297-326).

In principle both dicotyledonous and monocotyledonous plants that are amenable to transformation, can be modified by introducing a chimeric DNA construct according to the invention into a recipient cell and growing a new plant that harbours and expresses the foreign or endogenous DNA sequence.

Introduction and expression of foreign or chimeric DNA sequences in dicotyledonous (broad-leafed) plants such as tobacco, potato and alfalfa has been shown to be possible using the T-DNA of the tumour-inducing (Ti) plasmid of Agrobacterium tumefaciens (See, for example, Umbeck, U.S. Pat. No. 5,004,863, and International application PCT/US93/02480). A construct of the invention may be introduced into a plant cell utilising A. tumefaciens containing the Ti plasmid. In using an A. tumefaciens culture as a transformation vehicle, it is most advantageous to use a non-oncogenic strain of the Agrobacterium as the vector carrier so that normal non-oncogenic differentiation of the transformed tissues is possible. It is preferred that the Agrobacterium harbours a binary Ti plasmid system. Such a binary system comprises (1) a first Ti plasmid having a virulence region essential for the introduction of transfer DNA (T-DNA) into plants, and (2) a chimeric plasmid. The chimeric plasmid contains at least one border region of the T-DNA region of a wild-type Ti plasmid flanking the nucleic acid to be transferred. Binary Ti plasmid systems have been shown effective to transform plant cells as, for example, described by De Framond (1983, Biotechnology, 1:262) and Hoekema et al. (1983, Nature, 303:179). Such a binary system is preferred inter glia because it does not require integration into the Ti plasmid in Agrobacterium.

Methods involving the use of Agrobacterium include, but are not limited to: (a) co-cultivation of Agrobacterium with cultured isolated protoplasts; (b) transformation of plant cells or tissues with Agrobacterium; or (c) transformation of seeds, apices or meristems with Agrobacterium.

Recently, rice and corn, which are monocots, have been shown to be susceptible to transformation by Agrobacterium as well. Garlic and onion, which are also monocots, have been successfully transformed and regenerated by Agrobacterium mediated gene transfer (Rondo et al., 2000, Plant Cell Reports, 19(10): 989-993; Eady et al., 2000, Plant Cell Reports, 19(4): 376-381). However, many other important monocot crop plants, including oats, sorghum, millet, and rye, have not yet been successfully transformed using Agrobacterium-mediated transformation. The Ti plasmid, however, may be manipulated in the future to act as a vector for these other monocot plants. Additionally, using the Ti plasmid as a model system, it may be possible to artificially construct transformation vectors for these plants. Ti plasmids might also be introduced into monocot plants by artificial methods such as microinjection, or fusion between monocot protoplasts and bacterial spheroplasts containing the T-region, which can then be integrated into the plant nuclear DNA.

In addition, gene transfer can be accomplished by in situ transformation by Agrobacterium, as described by Bechtold et al. (1993, C.R. Acad. Sci. Paris, 316:1194). This approach is based on the vacuum infiltration of a suspension of Agrobacterium cells.

Alternatively, foreign or chimeric nucleic acids may be introduced using root-inducing (Ri) plasmids of Agrobacterium as vectors.

Cauliflower mosaic virus (CaMV) may also be used as a vector for introducing of exogenous nucleic acids into plant cells (U.S. Pat. No. 4,407,956). CaMV DNA genome is inserted into a parent bacterial plasmid creating a recombinant DNA molecule that can be propagated in bacteria. After cloning, the recombinant plasmid again may be cloned and further modified by introduction of the desired nucleic acid sequence. The modified viral portion of the recombinant plasmid is then excised from the parent bacterial plasmid, and used to inoculate the plant cells or plants.

Foreign or chimeric nucleic acids can also be introduced into plant cells by electroporation as, for example, described by Fromm et al. (1985, Proc. Natl. Acad. Sci., USA, 82:5824) and Shimamoto et al. (1989, Nature 338:274-276). In this technique, plant protoplasts are electroporated in the presence of vectors or nucleic acids containing the relevant nucleic acid sequences. Electrical impulses of high field strength reversibly permeabilise membranes allowing the introduction of nucleic acids. Electroporated plant protoplasts reform the cell wall, divide and form a plant callus.

Another method for introducing foreign or chimeric nucleic acids into a plant cell is high velocity ballistic penetration by small particles (also known as particle bombardment or microprojectile bombardment) with the nucleic acid to be introduced contained either within the matrix of small beads or particles, or on the surface thereof as, for example described by Klein et al. (1987, Nature 327:70). Although typically only a single introduction of a new nucleic acid sequence is required, this method particularly provides for multiple introductions.

Alternatively, foreign or chimeric nucleic acids can be introduced into a plant cell by contacting the plant cell using mechanical or chemical means. For example, a nucleic acid can be mechanically transferred by microinjection directly into plant cells by use of micropipettes. Alternatively, a nucleic acid may be transferred into the plant cell by using polyethylene glycol which forms a precipitation complex with genetic material that is taken up by the cell.

There are a variety of methods known currently for transformation of monocotyledonous plants. Presently, preferred methods for transformation of monocots are microprojectile bombardment of explants or suspension cells, and direct DNA uptake or electroporation as, for example, described by Shimamoto et al. (1989, supra). Transgenic maize plants have been obtained by introducing the Streptomyces hygroscopicus bar gene into embryogenic cells of a maize suspension culture by microprojectile bombardment (Gordon-Kamm, 1990, Plant Cell, 2:603-618). The introduction of genetic material into aleuron protoplasts of other monocotyledonous crops such as wheat and barley has been reported (Lee, 1989, Plant Mol. Biol. 13:21-30). Wheat plants have been regenerated from embryogenic suspension culture by selecting only the aged compact and nodular embryogenic callus tissues for the establishment of the embryogenic suspension cultures (Vasil, 1990, *Bio/Technol.* 8:429-434). The combination with transformation systems for these crops enables the application of the present invention to monocots. These methods may also be applied for the transformation and regeneration of divots. Transgenic sugarcane plants have been regenerated from embryogenic callus as, for example, described by Bower et al. (1996, *Molecular Breeding* 2:239-249).

Alternatively, a combination of different techniques may be employed to enhance the efficiency of the transformation process, e.g., bombardment with *Agrobacterium* coated microparticles (EP-A-486234) or microprojectile bombardment to induce wounding followed by co-cultivation with *Agrobacterium* (EP-A-486233).

10. Production and Characterisation of Differentiated Transgenic Plants

The methods used to regenerate transformed cells into differentiated plants are not critical to this invention, and any method suitable for a target plant can be employed. Normally, a plant cell is regenerated to obtain a whole plant following a transformation process.

Regeneration from protoplasts varies from species to species of plants, but generally a suspension of protoplasts is first made. In certain species, embryo formation can then be induced from the protoplast suspension, to the stage of ripening and germination as natural embryos. The culture media will generally contain various amino acids and hormones, necessary for growth and regeneration. Examples of hormones utilised include auxins and cytokinins. It is sometimes advantageous to add glutamic acid and proline to the medium, especially for such species as corn and alfalfa. Efficient regeneration will depend on the medium, on the genotype, and on the history of the culture. If these variables are controlled, regeneration is reproducible. Regeneration also occurs from plant callus, explants, organs or parts. Transformation can be performed in the context of organ or plant part regeneration as, for example, described in *Methods in Enzymology*, Vol. 118 and Klee et al. (1987, *Annual Review of Plant Physiology* 38:467). Utilising the leaf disk-transformation-regeneration method of Horsch et al. (1985, *Science,* 227:1229), disks are cultured on selective media, followed by shoot formation in about 24 weeks. Shoots that develop are excised from calli and transplanted to appropriate root-inducing selective medium. Rooted plantlets are transplanted to soil as soon as possible after roots appear. The plantlets can be repotted as required, until maturity is reached.

In vegetatively propagated crops, the mature transgenic plants are propagated by the taking of cuttings or by tissue culture techniques to produce multiple identical plants. Selection of desirable transgenotes is made and new varieties are obtained and propagated vegetatively for commercial use.

In seed propagated crops, the mature transgenic plants can be self-crossed to produce a homozygous inbred plant. The inbred plant produces seed containing the newly introduced foreign gene(s). These seeds can be grown to produce plants that would produce the selected phenotype, e.g., early flowering.

The transgenic plants of the invention include, but are not limited to, a transgenic T0 or R0 plant, i.e., the first plant regenerated from transformed plant cells, a transgenic T1 or R1 plant, i.e., the first generation progeny plant, and progeny plants of further generations derived therefrom which comprise and express the chimeric DNA construct.

Parts obtained from the regenerated plant, such as flowers, seeds, leaves, branches, fruit, and the like are included in the invention, provided that these parts comprise cells that have been transformed as described. Progeny and variants, and mutants of the regenerated plants are also included within the scope of the invention, provided that these parts comprise the introduced nucleic acid sequences.

It will be appreciated that the literature describes numerous techniques for regenerating specific plant types and more are continually becoming known. Those of ordinary skill in the art can refer to the literature for details and select suitable techniques without undue experimentation.

11. Characterisation

To confirm the presence of the foreign or endogenous DNA sequence in the regenerating plants, a variety of assays may be performed. Such assays include, for example, "molecular biological" assays well known to those of skill in the art, such as Southern and Northern blotting and PCR. A protein expressed by the heterologous DNA may be analysed by high performance liquid chromatography or ELISA (e.g., nptII) as is well known in the art.

12. Diagnostic Applications

The invention also extends to a method diagnosing a badnaviral infection of a plant, comprising detecting the presence in a cell or tissue of the plant of a nucleotide sequence that corresponds or is complementary to at least a portion of the sequence set forth in SEQ ID NO:1 or 2, or to a variant thereof, or an amino acid sequence that corresponds to at least a portion of the sequence set forth in SEQ ID NO:3, 4 or 5, or to a variant thereof.

12.1 Nucleic Acid-based Diagnostics

Nucleic acid used in polynucleotide-based assays can be isolated from cells contained in the biological sample obtained from a plant or plants part, according to standard methodologies (Sambrook, et al., "Molecular Cloning. A Laboratory Manual", Cold Spring Harbor Press, 1989; Ausubel et al., "Current Protocols in Molecular Biology", John Wiley & Sons Inc, 1994-1998). The nucleic acid may be genomic DNA or fractionated or whole cell RNA. Where RNA is used, it may be desired to convert the RNA to a complementary DNA. In one embodiment, the RNA is whole cell RNA; in another, it is poly-A RNA. In one embodiment, the nucleic acid is amplified by a nucleic acid amplification technique, as described for example in Section 3.

Depending on the format, the specific nucleic acid of interest is identified in the sample directly using amplification or with a second, known nucleic acid following amplification. Next, the identified product is detected. In certain applications, the detection may be performed by visual means (c.a., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994, *J Macromol. Sci. Pure, Appl. Chem., A*31(1): 1355-1376).

Following detection, one may compare the results seen in a given plant with a control reaction or a statistically significant reference group of normal plants. In this way, it is possible to correlate the amount of product expressed by the virus with the progression or severity of the infection.

12.2 Protein-based Diagnostics 12.2.1 Antigen-binding Molecules

Antigen-binding molecules that are immuno-interactive with a target molecule of the present invention can be used in the detection a TaBV polypeptide of the invention or a variant thereof. Thus, the present invention contemplates antigen-binding molecules that interact, for example, with an amino acid sequence corresponding to the sequence set forth in SEQ ID NO:3, 4 or 5. Illustrative assay strategies which can be used to detect a target polypeptide of the invention include, but are not limited to, immunoassays (e.g., Western blot or ELISA) involving the binding of an antigen-binding molecule to the target polypeptide in the sample, and the detection of a complex, which comprises the antigen-binding molecule and the target polypeptide.

Any suitable technique for determining formation of an antigen-binding molecule-target antigen complex may be used. For example, an antigen-binding molecule according to the invention, having a reporter molecule associated therewith may be utilised in immunoassays. Such immunoassays include, but are not limited to, radioimmunoassays (RIAs), enzyme-linked immunosorbent assays (ELISAs) and immunochromatographic techniques (ICTs), Western blotting which are well known those of skill in the art. For example, reference may be made to Coligan et at (1994, supra) which discloses a variety of immunoassays that may be used in accordance with the present invention. Immunoassays may include competitive assays as understood in the art or as for example described infra. It will be understood that the present invention encompasses qualitative and quantitative immunoassays.

13. Identification of Target Molecule Modulators

The invention also features a method of screening for an agent that modulates the expression of one or more of the TaBV open reading frames or variants thereof. The method comprises contacting a preparation comprising (i) at least a portion of the expression product or variant thereof, or (ii) at least a portion of a genetic sequence (e.g., a promoter), which regulates the expression of the open reading frame(s), in operable linkage with a reporter polynucleotide, with a test agent, and detecting a change in the level and/or functional activity of an expression product produced from (i) or (ii) relative to a normal or reference level and/or functional activity in the absence of said test agent.

Test agents contemplated by the present invention include agonists and antagonists of the ORFs and polypeptides described herein. Antagonists of include antisense molecules, ribozymes and co-suppression molecules as well as antibodies and inhibitor peptide fragments. Agonists include molecules which increase promoter activity or interfere with negative mechanisms.

Candidate agents encompass numerous chemical classes, though typically they are organic molecules, preferably small organic compounds having a molecular weight of more than 50 and less than about 2,500 Dalton. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogues or combinations thereof.

Small (non-peptide) molecule modulators of are particularly preferred. In this regard, small molecules are particularly preferred because such molecules are more readily absorbed after oral administration, have fewer potential antigenic determinants, and/or are more likely to cross the cell membrane than larger, protein-based pharmaceuticals. Small organic molecules may also have the ability to gain entry into an appropriate cell and affect the expression of a gene (e.g., by interacting with the regulatory region or transcription factors involved in gene expression); or affect the activity of a gene by inhibiting or enhancing the binding of accessory molecules.

Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogues. Screening may also be directed to known pharmacologically active compounds and chemical analogues thereof.

Screening for modulatory agents according to the invention can be achieved by any suitable method. For example, the method may include contacting a cell in which a polynucleotide corresponding to a TaBV ORF is expressed with an agent suspected of having said modulatory activity and screening for the modulation of the level and/or functional activity of a protein encoded by the polynucleotide, or the modulation of the level of an expression product encoded by the polynucleotide, or the modulation of the activity or expression of a downstream cellular target of the protein or the expression product. Detecting such modulation can be achieved using techniques including, but not restricted to, ELISA, cell-based ELISA, filter-binding ELISA, inhibition ELISA, Western blots, immunoprecipitation, slot or dot blot assays, immunostaining, RIA, scintillation proximity assays, fluorescent immunoassays using antigen-binding molecule conjugates or antigen conjugates of fluorescent substances such as fluorescein or rhodamine, Ouchterlony double diffusion analysis, immunoassays employing an avidin-biotin or a streptavidin-biotin detection system, and nucleic acid detection assays including reverse transcriptase polymerase chain reaction (RT-PCR).

It will be understood that a polynucleotide from which a target molecule of interest is regulated or expressed may be naturally occurring in the cell which is the subject of testing or it may have been introduced into the host cell for the purpose of testing. Further, the naturally-occurring or introduced sequence may be constitutively expressed—thereby providing a model useful in screening for agents which down-regulate expression of an encoded product of the sequence wherein the down regulation can be at the nucleic acid or expression product level or may require activation—thereby providing a model useful in screening for agents that up-regulate expression of an encoded product of the sequence. Further, to the extent that a polynucleotide is introduced into a cell, that polynucleotide may comprise the entire coding sequence which codes for a target protein or it may comprise a portion of that coding sequence (e.g. a domain such as a protein binding domain) or a portion that regulates expression of a product encoded by the polynucleotide (e.g., a promoter). For example, the promoter that is naturally associated with the polynucleotide may be introduced into the cell that is the subject of testing. In this embodiment, where only the promoter is utilised, detecting modulation of the promoter activity can be achieved, for example, by operably linking the promoter to a suitable reporter polynucleotide including, but not restricted to, green fluorescent protein (GIP), luciferase, β-galactosidase and catecholamine acetyl transferase (CAT). Modulation of expression may be determined by measuring the activity associated with the reporter polynucleotide.

In another example, the subject of detection could be a downstream regulatory target of the target molecule, rather than target molecule itself or the reporter molecule operably linked to a promoter of a gene encoding a product the expression of which is regulated by the target protein.

These methods provide a mechanism for performing high throughput screening of putative modulatory agents such as proteinaceous or non-proteinaceous agents comprising synthetic, combinatorial, chemical and natural libraries. These methods will also facilitate the detection of agents which bind either the polynucleotide encoding the target molecule or which modulate the expression of an upstream molecule, which subsequently modulates the expression of the polynucleotide encoding the target molecule. Accordingly, these methods provide a mechanism of detecting agents that either directly or indirectly modulate the expression and/or activity of a target molecule according to the invention.

In order that the invention may be readily understood and put into practical effect, particular preferred embodiments will now be described by way of the following non-limiting examples.

EXAMPLES

Example 1

Virus Purification and Nucleic Acid Extraction

Taro leaves showing symptoms of Alomae disease were collected from Lae, Papua New Guinea (PNG), and were either used fresh or stored at −80° C. for up to 6 months before use. TaBV was purified from leaves and petioles using the method described by Lockhart and Autrey, *Plant Disease* 72:230-233, 1988. DNA was purified from the virions as described by Harper and Hull in *Virus Genes* 17:271-278, 1998, and was resuspended in TE, pH 8.0.

Example 2

Total Plant Nucleic Acid Extraction

Total nucleic acid was extracted from both leaf and petiole tissue. The extraction buffer was prepared freshly by mixing equal volumes of buffer A (0.35 M sorbitol, 2% N-laurylsarcosine, 0.1 M Tris-HCl, pH 7.2, 4% (w/v) sodium metabisulphite) and buffer B (2 M NaCl, 0.04 M EDTA, 2% cetyltrimethylammonium bromide (CTAB), 0.1 M Tris-HCl pH 7.2). Taro tissue was ground in liquid nitrogen, and added to the extraction buffer at rate of 25 mg/mL buffer. An equal volume of chloroform was added, and the mixture incubated at 55° C. for 10 min. Following centrifugation (1000 g/15 min), the supernatant was re-extracted with chloroform and the nucleic acid precipitated with an equal volume of isopropanol. Nucleic acid pellets were washed with 70% ethanol and resuspended in 100 µl TE containing RNase A (1 mg/mL).

Example 3

PCR, Cloning and Sequencing

Two degenerate primers, BadnaFP and BadnaRP were designed based on the consensus sequences of the reverse transcriptase (RT) region and RNase H regions of published badnavirus sequences.

```
                                    SEQ ID NO: 10
Badna FP    5' ATGCCITTYGGIAARAAYGCICC 3'

SEQ ID NO: 11
Badna RP    5' CCAYTTRCAIACISCICCCCAICC 3'
```

DNA was amplified in 50 µL reactions containing 40 pmol of each degenerate primer, 10 mM Tris-HCl pH 8.3, 1.5 mM MgCl$_2$, 50 mM KCl, 200 µM dNTPs and 1U Taq DNA polymerase (Roche) and partially purified virion preparation as template. The amplification cycle conditions were 94° C. for 7 min, followed by 40 cycles of 94° C. for 30 s, 50° C. for 30 s, 72° C. for 30 s, and a final extension for 72° C. for 7 min. The amplified PCR product was cloned into pGEM-T (Promega pGEM®-T and pGEM®-T Easy vector system) according to the manufacturer's instructions.

Primers 1F and TRBR were used in a PCR reaction to amplify a region spanning part of the RT-coding region to the putative tRNA binding site.

```
                                    SEQ ID NO: 12
1F          5' GGATGCAGTATTCAAAGGGTGTG 3'

SEQ ID NO: 13
TRBR        5' CTGCAGGCGGCCGCGCTCTGATACCA 3'
```

Primer 1F and TRBR were designed from sequences derived from the BadnaFP/BadnaRP amplification product (with the inclusion of an Nco I restriction site) and the consensus sequence of the putative tRNA binding site of badnaviruses (with the additional of an anchor region which included a Pst I restriction site), respectively. The Expand™ Long Template PCR system (Buffer 1, Roche) was used according to the manufacturer's protocol with the PCR mix containing 0.4 µM of each specific primer and using total nucleic acid extracts as templates. The amplification conditions were 94' C for 4 min, followed by 10 cycles of 94° C. for 10 s, 37' C for 30 s and 68° C. for 8 min, 25 cycles of 94° C. for 10 s, 55° C. for 30 s and 68° C. for 8 min (with 20 s increments/cycle) and a final extension for 68° C. for 7 min. The resulting PCR product was A-tailed using Taq DNA polymerase (Roche) at 72° C. for 30 min, and again cloned into pGEM-T vectors.

Primers 5F and G2R were derived from the sequence of the 1F/TRBR amplified product and were used to amplify the remainder of TaBV genome.

```
                                    SEQ ID NO: 14
5F          5' AGTCTTTCCTTTGAGCTTGAGC 3'

SEQ ID NO: 15
G2R         5' CACACCCTTTGAATACTGCATCCAT 3'
```

The amplification was optimised using the Opti-Prime™ PCR optimisation system (Stratagene) with the Pwo/Taq DNA polymerase blend supplied in the Expand™ Long Template PCR kit (Roche). To reduce the chance of aberrant background in the amplification, purified viral DNA was used as template. The amplification cycle conditions were 94' C for 2 min, 20 cycles of 94° C. for 10 s, 50° C. for 30 s and 68° C. for 8 min, 20 cycles of 94° C. for 10 s, 55° C. for 30 s and 68° C. for 8 min. (with 20 s increments/cycle), and a final extension for 68° C for 7 min. The resulting PCR product was A-tailed and cloned as described above.

Plasmid templates for each of the cloned products were purified using standard alkaline lysis (39). Sequencing reactions were then prepared using the ABI PRISM® BigDye™ Primer Cycle Sequencing Kits (Applied Biosystems) and the reactions purified by sodium acetate precipitation. The final precipitated products were then sent for gel separation analysis at the Australian Genome Research Facility (AGRF), University of Queensland.

Example 4

Sequence Analysis

Sequence assembly and contig analysis of all the clones were performed with the aid of the computer software, SeqMan II Version 4.06, included in the Lasergene 99 Suite DNASTAR, The sequence of TaBV was analysed for the presence of open reading frames (ORFS), and the deduced amino acid sequences of the corresponding ORB were created using the EditSeq™ program (in DNASTAR). Nucleotide and deduced amino acid sequences of TaBV and other badnaviruses were aligned and compared using the MegAlign™ program (in DNASTAR). TaBV nucleotide sequence was analysed for potential promoter elements including TATA box and other cis-acting regulatory elements using either. EditSeq™ (in DNASTAR) and/or Search CARE included in the PlantCARE website (http://sphinx.rug.ac.be:8080/PlantCARE/) by which the query sequence was compared against the database of plant promoters and their cis-acting regulatory elements (Rombauts et al., *Nucleic Acid Research* 27:295-296, 1999). Analysis for putative polyadenylation (poly A) signals was performed using the POLYA SCAN program included in the GENE REGULATION website (http://www.gene-regulation.com) by which the query sequence was compared against the TRANSFAC database, a database on transcription factors, their genomic binding site and DNA-binding profiles (Wingender et al., *Nucleic Acid Research* 28:316-319, 2000).

Example 5

Purification of TaBV

Prior to purification of TaBV, leaf dips were prepared from Alomae-diseased taro and examined by electron microscopy. Small numbers of bacilliform virus particles, approximately 125-130 nm×25-40 nm, were observed in most plants, and tissue from these plants was pooled and used for virus purification. Examination of purified preparations revealed very few particles and attempts to trap these particles by immunosorbent electron microscopy using antiserum raised against a pool of SCBV isolates was unsuccessful.

Cloning of TaBV DNA

Initial attempts to obtain a full-length clone of the TaBV genome by conventional cloning were unsuccessful due to the inability to extract sufficient quantities of DNA from the low concentration of purified virions. Therefore, a PCR-based strategy was used to obtain the complete genome sequence.

The two degenerate primers, Badna FP (SEQ ID NO:10) and Badna RP (SEQ ID NO:11), described above, were used in a PCR with purified virions as template. The expected size product of approximately 600 by was amplified and cloned. Three clones were sequenced, and all three were found to contain inserts of 579 bp; at most, there were two nucleotide changes between the sequences. Two further primers, 1F (SEQ ID NO:12) and TRBR (SEQ ID NO:13), were subsequently designed from the consensus sequences derived from the 5'end of the three BadnaFP/BadnaRP PCR clones and the putative tRNA binding site of badnaviruses, respectively. Using total taro nucleic acid as template, the expected size product of approximately 1.9 kbp was amplified and cloned. Three clones were selected for sequencing and were found to contain inserts of 1900, 1901 and 1902 bp. When the sequences were compared, there was a minimum of 98.3% similarity at the nucleotide level. Primers 5F (SEQ ID NO:14) and G2R (SEQ ID NO:15) were used to obtain the remainder of the genome. These were used in a PCR with purified viral DNA as template and the expected size product of approximately 5.6 kbp was amplified. Two clones were sequenced and were found to contain inserts comprising 5671 bp and 5675 bp. At the nucleotide level, there was 99.5% similarity between the sequences.

Example 6

Complete Genomic Sequence

The complete TaBV genomic sequence was derived from the consensus sequences of Badna FP/Badna RP, 1F/TRBR-derived clones, and the 5671 bp 5F/G2R-derived clone. This latter clone was chosen because it was deemed to represent the minimal length of viral sequence found in infected plants. The complete sequence of the PNG isolate of TaBV comprised 7458 by and had a G+C content of 39.3%. The conserved plant cytoplasmic initiator methionine tRNA (tRNA$^{met}$) binding site was identified in the TaBV genome:

```
                                              SEQ ID NO: 16
    tRNA^met binding site     5' TGGTATCAGAGC 3'
``` and the numbering of the TaBV genomic sequence is consistent with other badnaviruses, beginning at the first nucleotide of the putative tRNA$^{met}$-binding site.

A map showing the genomic organisation of TaBV is provided as FIG. 1.

Example 7

Cloning of the TaBV-derived Promoter Fragments

Figure 2:
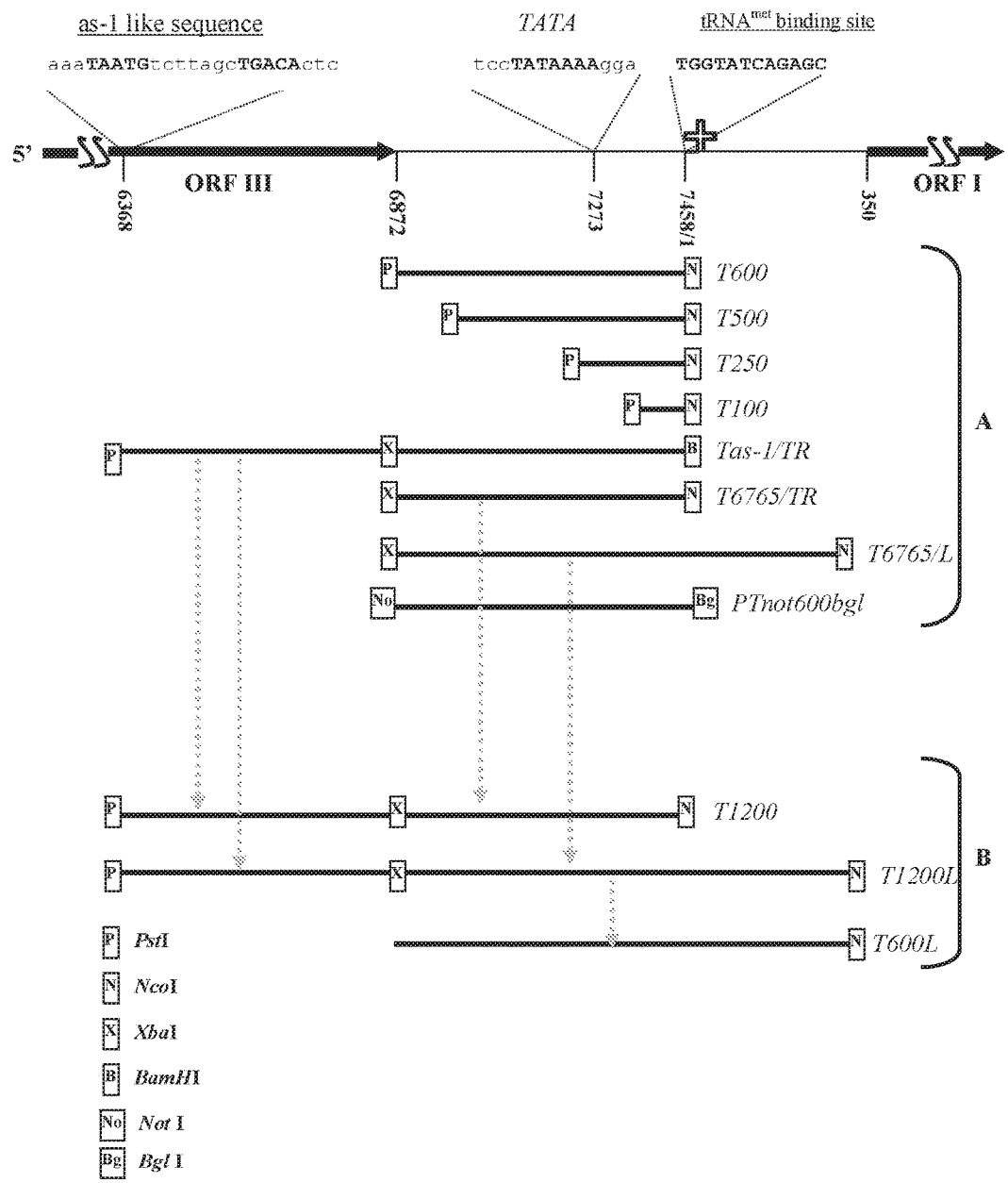
FIG. 2 is a diagrammatic representation of the TaBV genomic region, from which the promoter fragments were derived. Positions and sequences of a region resembling the CaMV 35S promoter as-1 element and of putative TATA box and tRNA$^{met}$ binding site are indicated by dash lines. The predicted position of open reading frame 1 (ORF 1) and ORF 3 are also indicated. All promoter fragments within bracket A were created with restriction sites as indicated by labelled boxes, except for the XbaI site which exists within the native TaBV sequence. Promoter fragments within bracket B were generated by directional cloning of fragments in bracket A, as indicated by grey arrows using indicated restriction sites. Promoter fragment T600L was generated by removal of the Pst I /Xba I fragment from T1200L and, in the process, destroying the Xba I site (SEQ ID NOS 31-33 disclosed respectively in order of appearance).

Two recombinant plasmids, one containing the TaBV genomic region spanning from 3' terminus of RT-coding region to the putative tRNA binding site and the other one containing the remainder of TaBV genomic region, were used as templates to create TaBV-derived promoters using PCR. Sizes of PCR products, PCR primers, TaBV genomic region targeted for PCR amplification and the cloning strategy are listed in Table 1 and illustrated schematically in FIG. 2A.

TABLE 1

| Designation | Size (bp) | Position start/end of TaBV genome | Primers forward/reverse | Primer sequence Sequence ID Number |
|---|---|---|---|---|
| T600 | 598 | 6873/12 | F-GTN/ | 5'CTGCAGATAGGATTCTTTGTGTGTG SEQ ID NO: 17 |
| | | | R-GTN | 5'CCATGGGCTCTGATACCAAGGTAG SEQ ID NO: 18 |

TABLE 1-continued

| Designation | Size (bp) | Position start/end of TaBV genome | Primers forward/reverse | Primer sequence Sequence ID Number |
|---|---|---|---|---|
| T500 | 529 | 6942/12 | P527-F/ | 5'CTGCAGGGACGCCACTAGGC SEQ ID NO: 19 |
| | | | R-GTN | 5'CCATGGGCTCTGATACCAAGGTAG SEQ ID NO: 18 |
| T250 | 260 | 7211/12 | P257-F/ | 5'CTGCAGGCCACCTCATCGGTTGC SEQ ID NO: 20 |
| | | | R-GTN | 5'CCATGGGCTCTGATACCAAGGTAG SEQ ID NO: 18 |
| T100 | 115 | 7356/12 | P114-F/ | 5'CTGCAGGAGCTTGAGCTTGTGTG SEQ ID NO: 21 |
| | | | R-GTN | 5'CCATGGGCTCTGATACCAAGGTAG SEQ ID NO: 18 |
| Tas-1/TR | 1190 | 6281/12 | FP-as-1/ | 5'CTGCAGGCCTTCACGGGTTAGATG SEQ ID NO: 22 |
| | | | TRBR-Bam | 5'GGATCCGCTCTGATACCAAGGTAG SEQ ID NO: 23 |
| T6765/TR | 706 | 6765/12 | FP-6765-pro/ | 5'CTGCAGGGGGAGATTGGCTGC SEQ ID NO: 24 |
| | | | R-GTN | 5'CCATGGGCTCTGATACCAAGGTAG SEQ ID NO: 18 |
| PTnot600 bgl | 598 | 6873/12 | P600Not-F/ | 5'GGAAGCTTGCGGCCGCCGAGAAGGTTCG SEQ ID NO: 25 |
| | | | P600Bgl-R | 5'GCGGAAGATCTTGCTCTGATACCAAGGTAG SEQ ID NO: 26 |
| T6765L | 1029 | 6765/335 | FP-6765-pro/ | 5'CTGCAGGGGGAGATTGGCTGC SEQ ID NO: 24 |
| | | | RP-leader | 5'CCATGGATCATATAATTGTAAGGTCGC SEQ ID NO: 27 |

The Expand™ PCR system (Boehringer) was used according to the manufacturer's protocol with the PCR mix containing 0.4 µM of each primer and 20-40 ng plasmid DNA as template. The amplification cycle conditions were 94° C. for 2 min, followed by 10 cycles of [94° C. for 10 s, 50° C. for 30 s and 68° C. for 5 min], 30 cycles of [94° C. for 10 s, 55° C. for 30 s and 68° C. for 8 min] and a final extension for 68° C. for 10 min. The resulting PCR products were A-tailed using Taq DNA polymerase (Roche) at 72° C. for 30 min, purified using High Pure PCR Product Purification Kit (Roche) and cloned into pGEM®-T easy vector (Promega) according to the manufacturer's protocol. Plasmids containing cloned fragments are referred to according to their designated name in Table 1 and FIG. 2A. For example, pGEM®-T containing the T600 fragment was named pGEM-T600. All clones were sequenced in both directions using an ABI PRISM® BigDye™ Terminator Cycle Sequencing Ready Reaction Kit (PE Applied Biosystems) and automated sequencer at the Australian Genome Research. Facility (AGRF), University of Queensland, Australia. Initially, the primers used to amplify the fragments from TaBV genomic clones were used as sequencing primer. For longer fragments internal primers were also used.

Example 8

Construction of Transformation Plasmids

Figure 3:
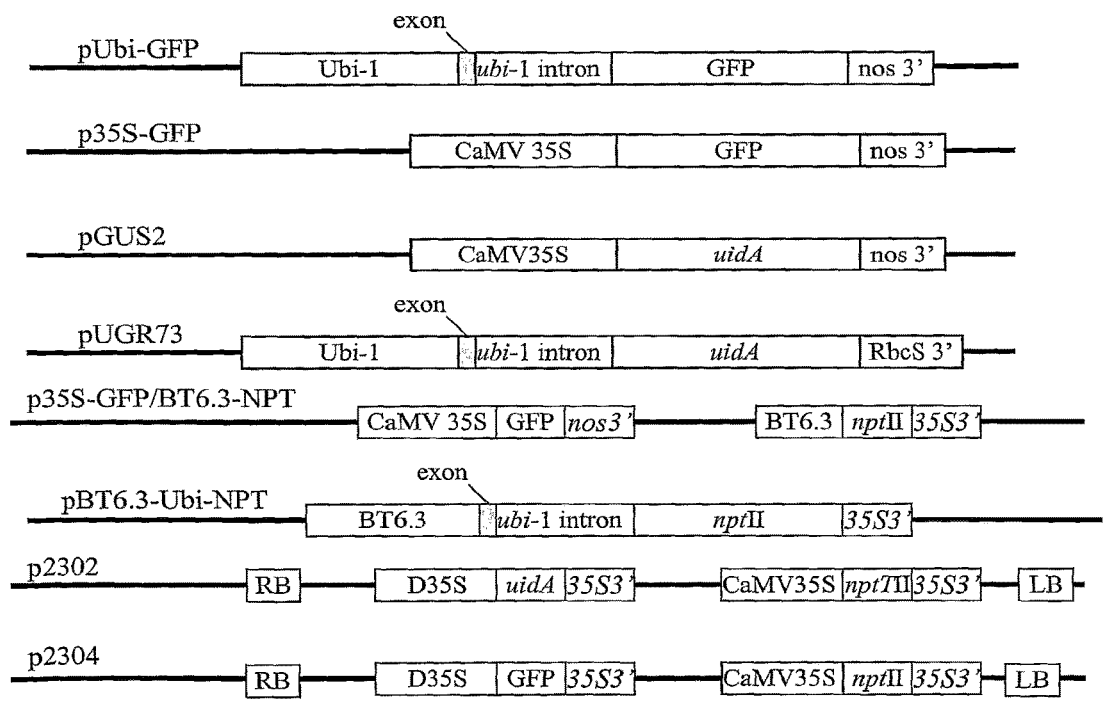
FIG. 3 is a schematic representation of plasmids used for either comparison of commonly used promoters with TaBV derived promoters and/or as selectable markers. Ubi-1=promoter region from maize polyubiquitin-1 gene, Ubi-1 intron=first exon and intron from maize polyubiquitin-1 gene, GFP=gene coding for green fluorescent protein, nos 3'=3' untranslated region from gene coding for *Agrobacterium tumefaciens* nopaline synthase, CaMV 35S=promoter region from gene coding for cauliflower mosaic virus (CaMV) 35S RNA, uidA=gene coding for β-glucuronidase (GUS), RbcS 3'=3' translated region from gene coding for *Nicotiana tabacum* rubisco, BT6.3=promoter region from DNA-6 from banana bunchy top virus (Dugdale et al 1998), nptII=gene coding for neomycin phosphotransferase, 35S 3'=3' untranslated region from gene coding for CaMV virus 35S RNA, D35S=double CaMV 35S promoter, RB=right border of binary vector T-DNA region, LB=left border of binary vector T-DNA region.

The TaBV promoter fragments were subsequently fused to reporter genes coding for either GUS or GFP, generating transformation constructs for microprojectile bombardment and Agrobacterium-mediated transformation. The organisation of promoter fragments that were not directly PCR generated from TaBV genomic clone but instead were derived from the original PCR fragments are illustrated diagrammatically in FIG. 2B. All plasmids which were provided by others and, used directly in transformation experiments, are illustrated diagrammatically in FIG. 3. Plasmids p35S-GFP, pUbi-GFP, p35S-GFP/BT6.3-NPT and pBT6.3-Ubi-NPT were supplied by the Centre for Molecular Biotechnology, Queensland University of Technology, Australia. Plasmids p35S-GFP and pUbi-GFP were used as positive controls for comparisons of GFP expression directed by different promoters. The plasmid p35S-GFP/BT6.3-NPT was used as a CaMV35S-GFP control in plants stably transformed using particle bombardment while pBT6.3-Ubi-NPT was used for co-transformation with other test and control plasmids that did not contain a selectable marker (Becker et al., *Plant Cell Rep* 19:229-234; Dugdale et al., *J Gen Virol* 79:2301-2311, 1998) Plasmids used for comparisons of GUS expression directed by different promoters were pGUS2 and pUGR73 (Christensen and Quail, *Transgenic Res* 5:213-218, 1996). Binary vectors p2302 and p2304 were used as positive controls and were supplied by the Centre for Molecular Biotechnology, Queensland University of Technology, Australia.

For the construction of transformation plasmids for microprojectile bombardment, all restriction enzyme digested promoter fragments and vectors were either gel purified using QIAquick® Gel Extraction Kit (QIAGEN) or directly purified after PCR using High Pure PCR Product Purification Kit (Roche) according to the manufacturers' protocols. One unit of T4 DNA ligase (Promega) was used for each ligation according to the manufacturer's protocol. The vectors pGEM-BS2P-GFP-NOS and pBaI-S-GUS-Rbc were also supplied by the Centre for Molecular Biotechnology, Queensland University of Technology, Australia. The plasmid pGEM-BS2P-GFP-NOS contained a promoter derived from banana bunchy top virus upstream of GFP and a NOS terminator, The plasmid pBaI-S-GUS-Rbc contained a promoter derived from the banana actin gene upstream of GUS and the terminator from the tobacco ribisco gene. These promoter fragments were removed from both pGEM-BS2P-GFP-NOS and pBaI-S-GUS-Rbc by PstI/NcoI digestion to allow for insertion of the TaBV derived promoters as PstI/NcoI fragments. The PstI/NcoI fragments of promoter clones (pGEM-T600, pGEM-T500, pGEM-T250, pGEM-T100) were subcloned into PstI/NcoI digested vectors, pGEM-BS2P-GFP-NOS and pBaI-S-GUS-Rbc, creating pT600-GFP, pT600-GUS, pT500-GFP, pT500-GUS, pT250-GFP, pT250-GUS, pT100-GFP and pT100-GUS, respectively. The PstI/XbaI fragment from pGEM-Tas-1/TR was placed upstream of the XbaI/NcoI fragment from pGEMT-6765/TR in a single directional cloning step into PstI/NcoI digested vectors, pGEM-BS2P-GFP-NOS and pBaI-S-GUS-Rbc, respectively, creating pT1200-GFP and pT1200-GUS.

Using the same cloning strategy, the PstI/XbaI fragment from pGEM-Tas-1/TR was placed upstream of XbaI/NcoI digested pGEM-T6765L into PstI/NcoI digested, pGEM-BS2P-GFP-NOS and pBaI-S-GUS-Rbc, to create pT1200L-GFP and pT1200L-GUS. The plasmids pT1200L-GFP and pT1200L-GUS were PstI/XbaI digested to remove part of the 5' region of the promoter, blunt ended using T4 DNA polymerase (Boehringer) and subsequently re-ligated creating pT600L-GFP and pT600L-GUS. The Ubi-1 promoter was removed from pUGR73 using NotI and BglII leaving the Ubi-1 intron, GUS gene and RbcS terminator in place. The NotI/BglII fragment from pGEM-Tnot600bgl was then ligated into pUGR73 from which the Ubi-1 promoter had been removed, creating pT600UGR.

For the construction of plasmids for *Agrobacterium*-mediated transformation, constructs containing TaBV-derived promoter-GFP/GUS reporter genes-terminator expression cassettes were cloned into the binary vector, pCambia2300 (CAMBIA) which contained a multiple cloning site and a CaMV 35S promoter-nptII-CaMV 35S terminator expression cassette. The PstI/EcoRI digested fragments from pT1200-GFP, pT600-GFP and pT500-GFP were cloned into PstI/EcoRI digested pCambia2300, creating pCambiaT1200-GFP, pCambiaT600-GFP and pCambiaT500-GFP respectively. TaBV derived promoter fragments together with the GUS gene were removed from pT1200-GUS, pT600-GUS and pT500-GUS using PstI and SmaI. The Rbc S terminator region was removed from pT1200-GUS, using PstI and EcoRI. Both promoter GUS fragment and terminator region were cloned into PstI/EcoRI digested pCambia2300 in one step, creating pCambiaT1200-GUS, pCambiaT600-GUS and pCambiaT500.

Example 9

Plant Material

Tissue cultured taro plantlets (*Colocasia esculenta* var. *antiquorum*) were originally from Palau and supplied by Mary Taylor (SPC, Fiji). Explants were multiplied on media containing MS Salts, 100 mg l$^{-1}$ myo-inositol, 0.4 mg l$^{-1}$ thiamine-HCl, 30 g l$^{-1}$ sucrose, 1.0 mg l$^{-1}$ BAP 0.30 mg l$^{-1}$ NAA, and 2 g l$^{-1}$ Phytagel (Sigma), pH 5.6. Taro plantlets were maintained at 25° C. with a 16 h photoperiod.

The embryogenic suspension culture of banana cv Ladyfinger (*Musa* spp. AAB) was generated and maintained as described by Becker et al. (supra) with the exception that embryogenesis was induced on media containing 2,4-D at 2 mg/L instead of 4 mg/L.

The tobacco suspension culture was initiated and maintained as follows. Approximately 10 tobacco (*Nicotiana tabacum* cv. Dynes) seeds were placed in 50 mL of liquid media (MS salts, 100 mg/L myo-inositol, 0.5 mg/L nicotinic acid, 0.5 mg/L. pyridoxine, 0.4 mg/L thiamine, 200 mg/L glycine, 0.222 mg/l: 2,4-D, 30 g/L sucrose, pH 5.7) in a 250 mL Erlenmeyer flask, and cultured in the dark on an orbital shaker (70 rpm) at 25° C. Half the media was replaced with fresh media every 7 days. After two months, callus cells sloughed off into suspension were separated from the original seed material. Suspension cells were then cultured in the light (16 h photoperiod) and subcultured every 7 days adding 5 mL of cell suspension to 45 mL of fresh liquid media.

Example 10

Transient Activity in Taro, Tobacco and Banana

Leaves from tissue cultured taro plantlets were excised 2 h prior to transformation and placed in MS salts liquid media. The leaves were then placed abaxial side-up, transferred onto the media containing 25 mL of MS salts and 5 g l$^{-1}$ Phytagel (Sigma) in 90 mm diameter Petri dishes prior to microprojectile bombardment. Tobacco cells were prepared prior to bombardment as per Dugdale et al. (supra), and banana cells were prepared as per Becker et al. (supra). All transformation constructs used for microprojectile bombardment were prepared using a Bresapure Plasmid Maxi Kit (Geneworks) according to the manufacturer's instructions. Transient expressions of reporter genes in taro leaves were assessed 72 h post bombardment whereas in tobacco and banana the activity was assessed 48 h post bombardment.

Example 11

Banana and Tobacco Transformation and Regeneration

The stable transformation and regeneration of banana plants were essentially as described by Becker et al. (supra). Banana was co-transformed with TaBV promoter expression vectors and selectable marker expression vector (pBT6.3-Ubi-NPT) by mixing the plasmids at equimolar concentrations prior to coating of gold particles. Prior to tobacco transformation, *Agrobacterium* (strain AGL1) containing binary vectors were cultured at 28° C. in YT broth containing 100 µg/mL kanamycin and 200 µM acetosyringone. Stably transformed tobacco (*Nicotiana tabacum* cv. Samsun) were generated using leaf disk transformation essentially as described by Horsch et al. (In: Gelvin SB, Schilperoort RA (eds) *Plant Molecular Biology Manual*, Kluwer, Dordecht, 1998). Transgenic tobacco plants were regenerated on media containing 50 mg/L geneticin and, to kill residual *Agrobacterium*, 200 mg/L timentin.

Example 12

Analysis of Transgenic Plants

Total genomic DNA of lines of regenerated transgenic banana or tobacco was extracted from leaf material of 2-3-month-old tissue culture plants essentially as described by Stewart and Via (*Biotechniques* 14:748-750, 1993). Genomic DNA (10-15 µg) was digested with NcoI, for transgenic banana, or ApaI, for transgenic tobacco, electrophoresed in a 1% agarose gel, capillary-blotted onto a positively charged nylon blotting membrane (Roche) and baked for 2 h at 80° C. Prior to hybridisation, the membrane was blocked for 60 min at 42° C. with DIG Easy Hyb™ (Roche). A 1.8 kbp DNA probe containing the complete uidA gene sequence was PCR amplified and DIG-labelled, which was used to detect the presence of uidA gene in the genomic DNA restriction digested fragments. The PCR DIG Labelling Mix system (Boehringer) was used according to the manufacturer's protocol with the PCR mix containing 0.4 µM of each primer-GUS1 and GUS2:

```
                                    SEQ ID NO: 28
    GUS1         5' ATGTTTACGTCCTGT

SEQ ID NO: 29
    GUS2         5' TTACTTGTTTGC
``` and 40 ng PT600GR as template. The amplification cycle conditions were 94° C. for 4 min, followed by 35 cycles of [94° C. for 50 s, 50° C. for 50 s and 72° C. for 2 min], and a final extension for 2° C. for 10 min. The membrane was hybridised with DIG-labelled probe for 20 hr at 42° C., washed as described by Hermann et al. (*Plant Cell Rep* 20:525-530, 2001), and detected using CDP-STAR system (Roche) according to the manufacturer's instructions. Hybridisation signal was detected with CURIX ORTHO HT-G 100 NIF ECOPAC medical X-ray film (AGFA).

Example 13

Reporter Gene Assays and Detection

GFP expression was visualised using a Leica MZ12 stereo microscope with GFP-Plus fluorescence module. GUS activity was assayed histochemically and fluorometrically essentially as described by Jefferson et al. (*EMBO J* 6:3901-3907, 1987). Fluorescence was measured using a Perkin Elmer LS50B luminescence spectrophotometer.

Example 14

Cloning of Putative Promoter Sequences from TaBV Into Promoter-Reporter Constructs Sequence analysis of the TaBV genome led to the identification of putative promoter elements, such as a TATA box and sequences similar to CaMV as-1 sequence (Yin and Beachy, *Plant J* 7: 969-980, 1995). A region of the TaBV genome containing potential promoter elements was chosen to generate a series of promoter fragments by PCR which were then cloned into expression vectors upstream of either the GUS or GFP reporter genes.

Example 15

Transient Assays of TaBV Promoter Activity in Taro, Banana and Tobacco

Figure 4:
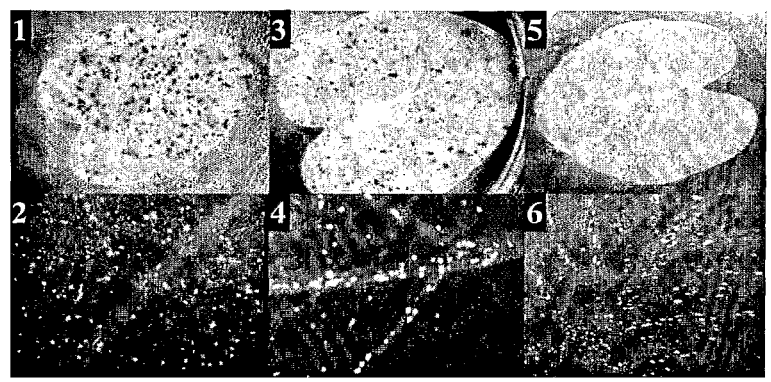
FIG. 4 is a photographic representation showing transient expression of uidA and GFP in taro directed by ubi1 promoter plus ubi1 intron (1, 2), CaMV 35S promoter (3, 4) and T600 promoter (5, 6).

Currently, there is no routine transformation system available for taro. Therefore, leaves from in vitro taro plantlets were used as microprojectile target tissue in transient assays. The activity of the TaBV-derived promoter fragments T100, T250, T500, T600, T600L, T1200 and T12001L were compared to that of the maize polyubiquitin-1 (Ubi-1) and cauliflower mosaic virus 35S (CaMV35S) promoters. Based on the presence of blue foci after histochemical GUS staining and also green fluorescent foci when GFP was used, T500, T600, T1200 and T1200L were active in taro leaf. The precise number of foci was not counted. However, these promoter fragments and the CaMV35S promoter appeared to result in a lower number of foci in comparison to Ubi-1 (FIG. 4). T100, T250 and T600L had no detectable activity.

Figure 5:
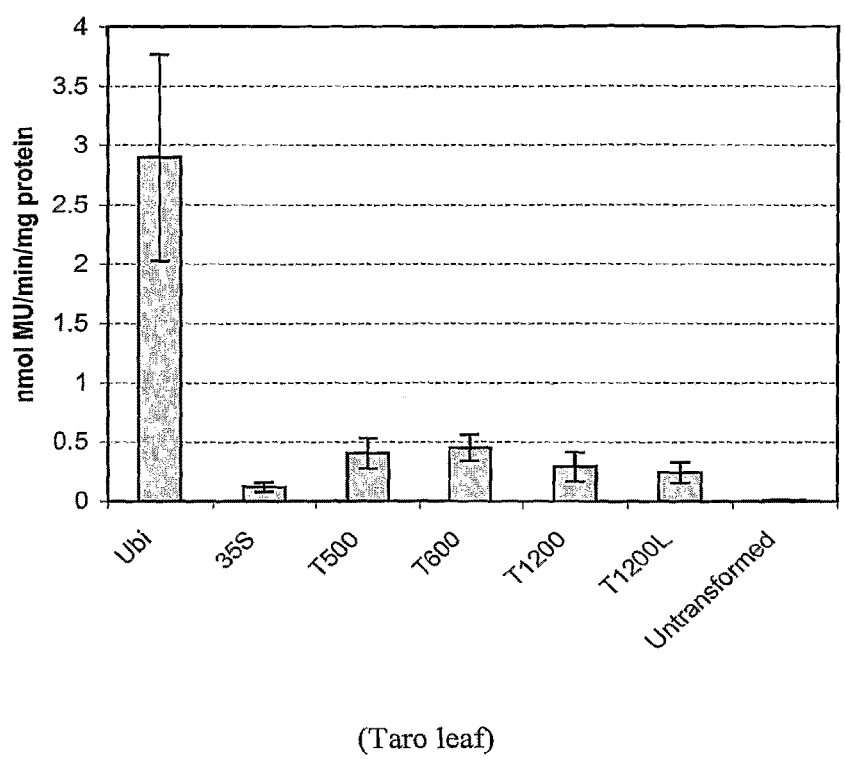
FIG. 5 is a histogram representing a comparison of transient promoter activity of TaBV-derived promoters with the maize polyubiquitin promoter (Ubi; in pUGR73) and the CaMV 35S promoter (35S; in pGUS2) in taro leaf using the uidA reporter gene. In vitro-grown taro leaves were bombarded with expression vectors and promoter activity assayed by GUS fluorometric assay 72 h post-bombardment. Values are expressed as the mean value of four replicates for each promoter construct, in nmol MU/min/mg total soluble protein, ±the standard error. TaBV derived promoters examined included T500 (in pT500-GUS), T600 (in pT600-GUS), T1200 (in pT1200GUS) and T1200L (in pT1200L-GUS). Non-bombarded leaves (untransformed) were also included a control for endogenous GUS activity.

The activity of TaBV-derived promoter fragments that were shown to direct expression in taro leaf was then quantified via fluorometric GUS assay. The result of this assay was consistent with that of the histochemical staining with the activity of T500, T600, T1200 and T1200L being similar to that of CaMV35S and approximately 10-15% of Ubi-1 (FIG. 5).

Promoter fragments T500, T600, T600 with Ubi-1 intron (T600U) and T1200 were all shown to be active in transient assays in banana suspension cells. Based on the number of blue foci (GUS) and green fluorescent foci (GFP) their activity appeared to be lower than that of Ubi-1 and CaMV35S. Interestingly, the addition of the Ubi-1 intron to T600 did not appear to enhance expression but rather resulted in a reduction.

In tobacco suspension cells, T500, T600 and T1200 promoter fragments were also active as indicated by the presence of many blue foci and green fluorescent foci. However, the number of foci did not appear to be as great as in cells bombarded with CaMV35S expression vectors.

Example 16

Activity of TaBV Promoter in Stably Transformed Banana and Tobacco

Figure 6:
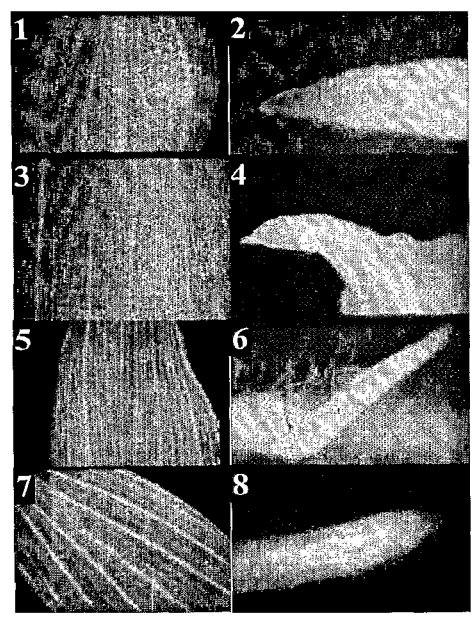
FIG. 6 is a photographic representation showing GFP expression in the roots and leaves of transgenic banana directed by the CaMV 35S promoter (1, 2), T1200 promoter (3, 4), T600 promoter (5, 6) and T500 promoter (7, 8).

Preliminary results from transient assays in banana and tobacco indicated that TaBV-derived promoter fragments T500, T600 and T1200 were active in a monocotyledonous (banana) and dicotyledonous (tobacco) species. Therefore, the activity of these promoter fragments in stably transformed banana and tobacco was assessed. In banana transformed with T500, T600, T1200 and CaMV35S GFP expression vectors, strong green fluorescence was observed in leaf, pseudostem and root tissue, whereas only the red fluorescence from chlorophyll was observed in non-transformed control plants (FIG. 6). There did not appear to be any difference in the pattern of expression between the different promoter fragments. All appeared to direct expression in a constitutive manner. However, green fluorescence was greater in newly emerged leaves and vascular tissue.

Figure 7:
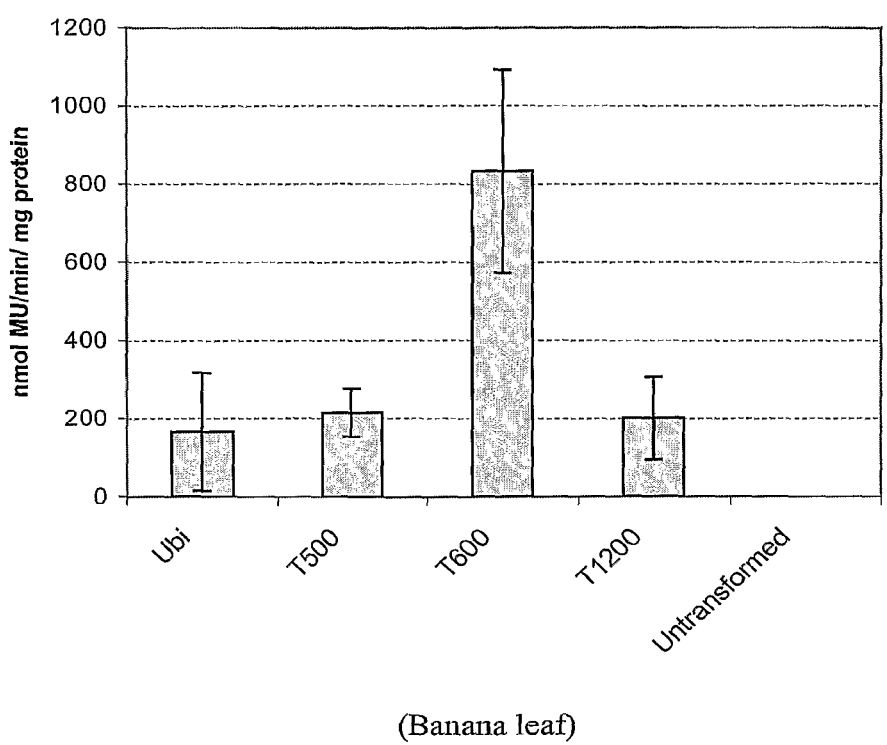
FIG. 7 is a histogram representing a comparison of TaBV derived promoter activity with the maize polyubiquitin promoter (Ubi; in pUGR73) in stably transformed banana leaf using the uidA reporter gene. Banana leaves from plants derived from independent transformation events (between 4 and 12 for each promoter construct) were assayed by GUS fluorometric assay. Values are expressed as the mean value, in nmol MU/min/mg total soluble protein, ±the standard error. TaBV derived promoters examined included T500 (in pT500-GUS), T600 (in pT600-GUS), T1200 (in pT1200-GUS). Non-bombarded leaves (untransformed) were also included a control for endogenous GUS activity.

To quantify the activity of the promoter fragments, between 4 and 12 transgenic banana lines were generated for each GUS expression vector. These lines were confirmed as being derived from individual transformation events by Southern blot analysis. Fluorometric GUS assays on these independent lines revealed that Ubi-1, T500 and T1200 all directed similar levels of expression while T600 activity was approximately four-fold greater than that of the other promoter fragments and Ubi-1 (FIG. 7).

Figure 8:
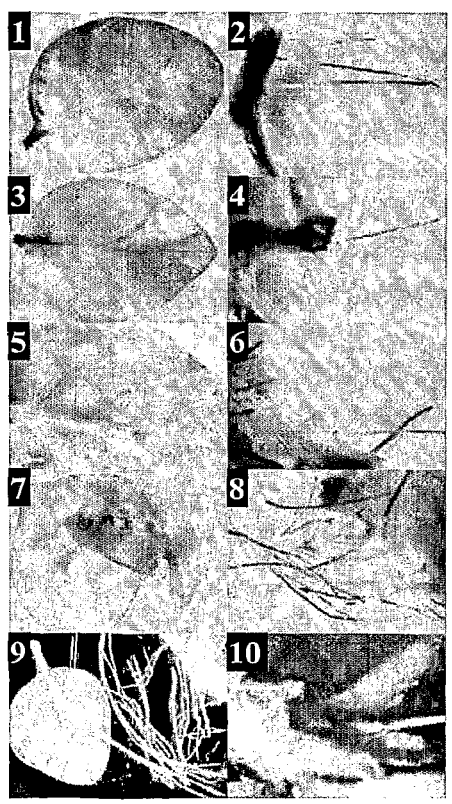
FIG. 8 is a photographic representation showing expression of uidA in transgenic tobacco directed by the CaMV 35S promoter (1, 2), T1200 promoter (3, 4), T600 promoter (5, 6) and 7500 promoter (7, 8). (9) Leaf and root of untransformed tobacco showed no uidA expression. (10) Transgenic tobacco showed GRP expression in newly emerging young leaves and roots.
Figure 9:
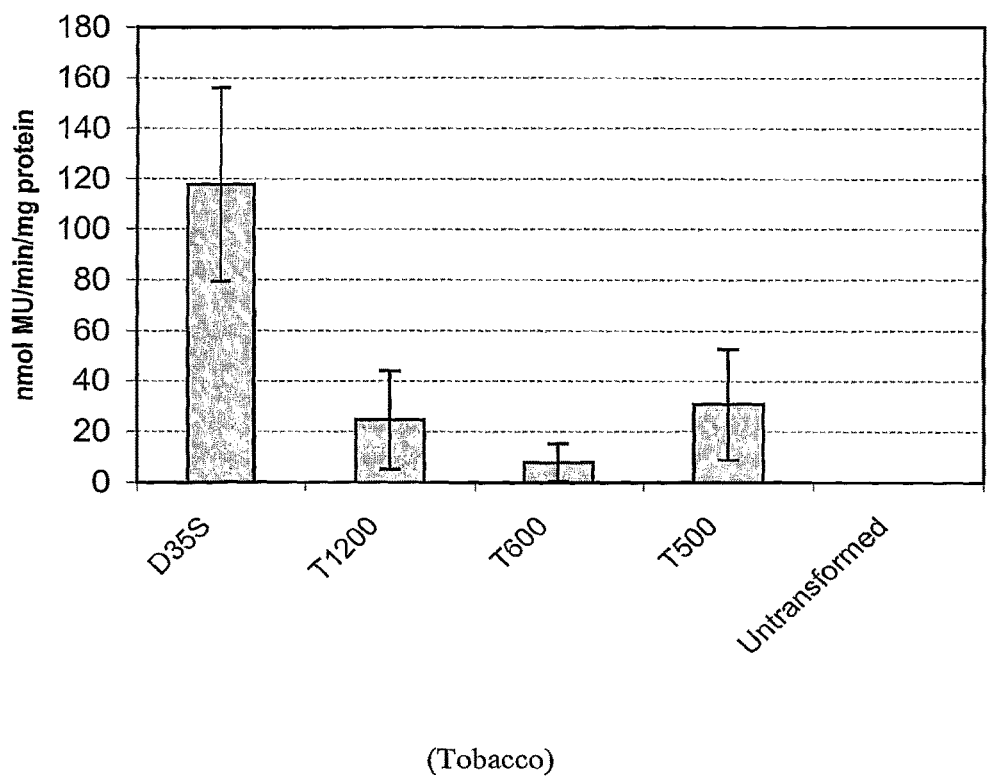
FIG. 9 is a histogram representing a comparison of TaBV derived promoter activity with the double CaMV promoter (D35S; in p2302) in stably transformed tobacco leaf using the uidA reporter 35S gene. Tobacco leaves from plants derived from independent transformation events (between 5 and 7 for each promoter construct) were assayed by GUS fluorometric assay. Values are expressed as the mean value, in nmol MU/min/mg total soluble protein, ±the standard error. TaBV derived promoters examined included 7500 (in pCambiaT500-GUS), T600 (in pCambiaT600-GUS), T1200 (in pCambiaT1200-GUS). Non-bombarded leaves (untransformed) were also included a control for endogenous GUS activity.

In transgenic tobacco, the pattern of GFP expression was difficult to determine due to the green fluorescence being obscured by bright red chlorophyll fluorescence. Therefore, the pattern of expression directed by the TaBV-derived promoter fragments was assessed by histochemically staining GUS transformed plant tissue. The double CaMV35S promoter and T500, T600 and T1200 promoter fragments all directed GUS expression in leaves, stems and roots (FIG. 8). More intense blue staining was observed in vascular tissue of the stem and in the root tips. Between. 5 and 7 transgenic tobacco lines were generated for each GUS expression vector. These lines were confirmed as being derived from individual transformation events by Southern blot analysis. Fluorometric GUS assays on these independent lines revealed that the activity of the double CaMV35S was, depending on the fragment length, between approximately four and ten-fold greater than the TaBV derived promoter fragments (FIG. 9).

Interestingly, the activity the TaBV-derived promoter fragments relative to each other was different in banana and tobacco. In banana, truncating the promoter region from T1200 to T600 resulted in increased expression. Further truncation from T600 to T500 reduced expression levels. In tobacco, the inverse was true where, to a lesser degree, truncating the promoter region from T1200 to T600 decreased expression levels and further truncation from T600 to T500 increased expression levels again.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

What is claimed is:

1. A chimeric DNA construct comprising a DNA molecule having promoter activity and operably linked to a foreign or endogenous DNA sequence to be transcribed, wherein the DNA molecule has at least 95% sequence identity, or hybridizes under high stringency conditions, to a biologically active fragment of the sequence set forth in SEQ ID NO:6, wherein the biologically active fragment comprises nucleotides 527 to 970 of SEQ ID NO:6, wherein the high stringency conditions comprise 1% BSA, 1 mM EDTA, 0.5 M NaHPO$_4$ (pH 7.2), and 7% SDS for hybridization at 65° C. and washing at 68° C. in 0.2×SSC, 0.1% SDS.

2. The construct of claim 1, further comprising a 3' non-translated sequence that is operably linked to the foreign or endogenous DNA sequence and that functions in plant cells to terminate transcription and/or to cause addition of a polyadenylated nucleotide sequence to the 3' end of a transcribed RNA sequence.

3. The construct of claim 1, wherein the foreign or endogenous DNA sequence encodes a structural or regulatory protein.

4. The construct of claim 1, wherein the foreign or endogenous DNA sequence encodes a transcript capable of modulating expression of a corresponding target gene.

5. The construct of claim 4, wherein the transcript comprises a transcribed region aimed at downregulating the expression of the corresponding target gene.

6. The construct of claim 4, wherein the transcript comprises a transcribed region that represents a molecule selected from the group consisting of a sense suppression molecule, an antisense RNA, a ribozyme and an RNAi molecule.

7. The construct of claim 1, further comprising a leader sequence which modulates mRNA stability.

8. The construct of claim 1, further comprising a targeting sequence for targeting a protein product of the foreign or endogenous DNA sequence to an intracellular compartment within plant cells or to an extracellular environment.

9. The construct of claim 1, further comprising a selectable marker gene.

10. The construct of claim 1, further comprising a screenable marker gene.

11. The construct of claim 1, wherein the nucleotide sequence is constitutively expressed in a host cell.

12. The construct of claim 11, wherein the host cell is a plant cell.

13. The construct of claim 11, wherein the host cell is a monocotyledonous plant cell.

14. The construct of claim 11, wherein the host cell is a non-graminaceous monocotyledonous plant cell.

15. The construct of claim 11, wherein the host cell is a non-graminaceous monocotyledonous plant cell selected from the group consisting of Musaceae, taro, ginger, onions, garlic, pineapple, bromeliads, palms, orchids, lilies and irises.

16. The construct of claim 11, wherein the host cell is a graminaceous monocotyledonous plant cell.

17. The construct of claim 11, wherein the host cell is a dicotyledonous plant cell.

18. A progeny obtained from a differentiated transgenic plant comprising a chimeric construct, wherein the progeny comprises the chimeric construct, and wherein the differentiated plant is produced by a method comprising:
(a) introducing into regenerable plant cells a chimeric DNA construct comprising a DNA molecule having promoter activity and operably linked to a foreign or endogenous DNA sequence to be transcribed, wherein the DNA molecule has at least 95% sequence identity, or hybridizes under high stringency conditions, to a biologically active fragment of the sequence set forth in SEQ ID NO:6, wherein the biologically active fragment comprises nucleotides 527 to 970 of SEQ ID NO:6, wherein the high stringency conditions comprise 1% BSA, 1 mM EDTA, 0.5 M NaHPO$_4$ (pH 7.2), and 7% SDS for hybridization at 65° C. and washing at 68° C. in 0.2×SSC, 0.1% SDS;
(b) identifying or selecting a population of transformed plant cells; and
(c) regenerating a differentiated transgenic plant from the population.

19. A plant part obtained from a differentiated transgenic plant produced by a method comprising the steps of:
(a) introducing into regenerable plant cells a chimeric DNA construct comprising a DNA molecule having promoter activity and operably linked to a foreign or endogenous DNA sequence to be transcribed, wherein the DNA molecule has at least 95% sequence identity, or hybridizes under high stringency conditions, to a biologically active fragment of the sequence set forth in SEQ ID NO:6, wherein the biologically active fragment comprises nucleotides 527 to 970 of SEQ ID NO:6, wherein the high stringency conditions comprise 1% BSA, 1 mM EDTA, 0.5 M NaHPO$_4$ (pH 7.2), and 7% SDS for hybridization at 65° C. and washing at 68° C. in 0.2×SSC, 0.1% SDS;
(b) identifying or selecting a population of transformed plant cells; and
(c) regenerating a differentiated transgenic plant from the population; wherein the plant part contains the chimeric construct.

20. A differentiated transgenic plant regenerated from transformed plant cells obtained by a method comprising the steps of:
(a) introducing into regenerable plant cells a chimeric DNA construct comprising a DNA molecule having promoter activity and operably linked to a foreign or endogenous DNA sequence to be transcribed, wherein the DNA molecule has at least 95% sequence identity, or hybridizes under high stringency conditions, to a biologically active fragment of the sequence set forth in SEQ ID NO:6, wherein the biologically active fragment comprises nucleotides 527 to 970 of SEQ ID NO:6, wherein the high stringency conditions comprise 1% BSA, 1 mM EDTA, 0.5 M NaHPO$_4$ (pH 7.2), and 7% SDS for hybridization at 65° C. and washing at 68° C. in 0.2×SSC, 0.1% SDS;
(b) identifying or selecting a population of transformed plant cells; and
(c) regenerating a differentiated transgenic plant from the population.

21. A transformed plant cell containing a chimeric DNA construct comprising a DNA molecule having promoter activity and operably linked to a foreign or endogenous DNA sequence to be transcribed, wherein the DNA molecule has at least 95% sequence identity, or hybridizes under high stringency conditions, to a biologically active fragment of the sequence set forth in SEQ ID NO:6, wherein the biologically active fragment comprises nucleotides 527 to 970 of SEQ ID NO:6, wherein the high stringency conditions comprise 1% BSA, 1 mM EDTA, 0.5 M NaHPO$_4$ (pH 7.2), and 7% SDS for hybridization at 65° C. and washing at 68° C. in 0.2×SSC, 0.1% SDS.

22. A differentiated transgenic plant comprising plant cells containing a chimeric DNA construct comprising a DNA molecule having promoter activity and operably linked to a foreign or endogenous DNA sequence to be transcribed, wherein the DNA molecule has at least 95% sequence identity, or hybridizes under high stringency conditions, to a biologically active fragment of the sequence set forth in SEQ ID NO:6, wherein the biologically active fragment comprises nucleotides 527 to 970 of SEQ ID NO:6, wherein the high stringency conditions comprise 1% BSA, 1 mM EDTA, 0.5 M $NaHPO_4$ (pH 7.2), and 7% SDS for hybridization at 65° C. and washing at 68° C. in 0.2×SSC, 0.1% SDS.

23. The transgenic plant of claim 22, wherein the plant is a dicotyledonous plant.

24. The transgenic plant of claim 22, wherein the plant is a monocotyledonous plant.

25. The transgenic plant of claim 22, wherein the plant is a graminaceous monocotyledonous plant.

26. The transgenic plant of claim 22, wherein the plant is a non-graminaceous monocotyledonous plant.

27. The transgenic plant of claim 22, wherein the construct comprises a selectable marker gene.

28. The transgenic plant of claim 22, wherein the construct comprises a screenable marker gene.

29. The transgenic plant of claim 22, wherein the expression of the chimeric DNA construct renders the differentiated transgenic plant identifiable over the corresponding non-transgenic plant.

* * * * *

SEQUENCE LISTING

<160> NUMBER OF SEQ ID NOS: 33

<210> SEQ ID NO 1
<211> LENGTH: 6523
<212> TYPE: DNA
<213> ORGANISM: Taro bacilliform virus

<400> SEQUENCE: 1

```
atggcaaaga aatttgaagc agctattaaa gactggtatg ataactctcg acgagcagat      60
ctttcctatc ttgacctagc caccactaca aaaccttctg catcacaatt agctcataat     120
ctacaagtca tttttgatag attatcctta cattcttcag tctccattaa ggaacattac     180
gaagtagtta gcaaacttca ttctttggaa aaatctatag aagaattaaa gtctgaattg     240
actacggtca aaagggcttt aacttctatc caaaagaag ttttcaccca caaacccctc      300
acagcacagg aagtgcaaac ccttgcacaa agtctgatca aagaacctaa gcaaatagaa     360
cagcaggccg tatttcttct aaaggagctt aaagaacaaa cagcaaaaat tcaagctttg     420
ctccacgagc ttaaaagttg atgtctgtac ctaattccac atacccaggg tacatcaaaa     480
gtttagaaga aacaaaagtc ttaggagatc catctgtagg attctctgaa attcctacca     540
ctgctatcgg aaccgctaca ggtttttcaa ctctttataa gcagaacaat acaatcatca     600
atctgcttat atctcttcat aaaaaggttg atagcctctc caaaaagaca gacgtcgacg     660
agttagccac tgagttgtcc aaactcacaa tcaaggatac cccaaaggtt aaggctaaaa     720
ctcctctata cgtcttcaag agtccccgtc ttatcctcga agaggaaaga tataaaatcg     780
gccttcctcc taccactacc gattggactt ggcctgtagg acatccttt gctcctccac      840 caaaaacatc cacaaaggca tccacctctt cttaaagatg tctttagcag ttcgtgatcg     900
tggttccaac ccttccacct cttctacagt ccctagtcag caggaccaga ttcgggatta     960
tagaaacatg caaagagttc gtcatacagc ggaaagagca gcaaggagaa tcttccctgg    1020
aagattcaat agaactctgg aatcacaaat caatccagag gcagaaatcc gtctttctca    1080
acaaagacga gcagcaatgg tcccagcaga agtattatac aatacttctc catcaacaag    1140
aaatcagaaa gtgtatcagc actattctga agaaagaatt ctttgtacag gacaaaatca    1200
gcaattaaat ttgccattta ttaatgaatc ttcttacaga gccctcagag aatcaggtca    1260
acagcatctt cacataggcc tgatcatgat tcgtgtacat cctcttcatc ggcgaaatgc    1320
aggaacgaca gctcttattg tccctcgaga cataagatgg aatgatgaca gatctatcat    1380
tggcaccatg gagatagatc tcagcgccgg atcccaaatt gtttatattg ccccaaatat    1440
catgctatct gttgaagatt tttatcgcaa catacaactt gcgattcaaa ctcagggcta    1500
```

```
tgaaaactgg aactctgccg agagtaactt gctcatctct cgcgctctta ttggtcgtct   1560
gacaaacgac agttttacag gattccagta caatatctct aatgttgctg agtacttgca   1620
cagtcatggt gtgcaagcta ttgaaggaca agctcatcca agaaccctcg gcaatcgatg   1680
gatcctacaa gcaccagcac caccaaggtc tctcgttcca caaaacgtgg agaccaccac   1740
tcttctggat ggtaatgtgt ctatacgttt ctccaattac catcaagcac cagttaatga   1800
tactcaggat aattctcatc ctgatatcca agaagacgaa aaccaattca ttggttttct   1860
ttctgatttg ggggaagaat atgaattgga gtatccttct ttcactccag ttcatgcaga   1920
tgaattcatt tttataatca ttaatgggga agaaattccc gatgattttg tctcatcttt   1980
ttgttccaat ttctctcctc caccaattcc agaaccagaa cccacagcca ttgaagaaac   2040
agcttttact ttggaagaac aattcaatga cctggactat cctaccctca tttcaatgga   2100
aaaacaatta gtccagtctt cagttacttc agcttacaac ccacccacag aacctcttat   2160
gggtcaggta gtctatccac cagcatctgc acctagacca caagctgaaa cttcttcaac   2220
ctctgaaaga ttcaaaaatt tcagagcaaa gccatatagt accccgacta ttttcctacc   2280
tccagcatac aatcaacaag gggctatatt agttcttcct gatgacattg cttatatga   2340 agataccatt tctcgttggg agtccattac tctcaacatg atgaatgaaa aggtttggcc   2400
atcaaatgaa gcaaaggcca aatatatgga aaatctctta ggagaaatgg agaagaagac   2460
atggatacaa tggaggacca catatgtatc cgaatatgat gctttggtcc aacaaagtga   2520
tgaaacacag aacctcctgt ctcaggtaag gaggatattt ctgctacaag acccatatca   2580
aggatcaact gcggaacaag atcaggcata taatgatctt gaaagaattt cttgtgataa   2640
tattaaggat ttaattcctt atctgattca gttccgcaat ttagctgcaa aatctggacg   2700
cttgttctta ggtccagaat tatctgaaaa attattcaga aaaatgccgc ctctaatagg   2760
caaagaaatt gaaacagcat tcatagcaaa gcatggtaat gcaaacatca ctgttatgcc   2820
tcgcattcat tttgcttacc attatcttgc tgaattatgt aaaaaggcag cattacagag   2880
atcattgaag gatctcagct ctgcaacca gattcctctc ccaggaatct atacaaaagg   2940
caacaagaag tttggtcttc gaaaggccag aacatacaaa ggaaaaccac atccaacaca   3000
tgtacgggta ttcaaaaagg caaaatacca gcgtacaaag aagtgcaaat gctttatatg   3060
tggtgaacca ggacattttg ctcgagaatg cacaaagcaa agaggaaata ttgtacgagc   3120
aacagtacat caagaactgg ccataccaga taattttgat gttgtttctg tggatgcaga   3180
tgaatctgac agctctggca tctacagtta ttccggaaaat gaagctcctc tgcaagaagt   3240
aaattctttc attcatgatg aaaatatctt tttcctatct gatgcagacg agtttgaaag   3300
cccacaacag catcttcatg aaacggtaaa tatgcttcaa tctagatctg cttatttacc   3360
tcaagtagct gttggagaag aaaaattgaa ttgtagtcac atttggctac aagatgttga   3420
tattccatct gataagcaca aatgccacac atgtagaaga gacactcaga aacattacag   3480
actggaatgt caaaaatgca aattcttggt ttgctcacta tgcacaattc catatctcgg   3540
aatcaccatg caattcaggc aaaagcaaaa atctcagcct gaaaacccaa acttagtccg   3600
agaattgtta gaacatgcca tttttctaga agaaaaatgc aaaaatcaag aattactgtc   3660
agaaactcag atagaaagga tagtcagttc tgaaaaacaa gtcaaatttt atggcatcct   3720
tcctacaaaa aagtccaaca aatctgctgg gtatgactta caatccaaca ttgatataga   3780
aatcccgcca ggaaaatgta cagtcatttc tactggaacc tttctacaaa tgcctgacaa   3840
```

```
catgtatggt agacttgtag aaagaacatc tttggcaata caggggatta cagtacaagg    3900
aggagtcatt gacccagact tcacaggaga aatacagatt gttctcttca atcataatac    3960
tgctccttat cctgtgaaga aaacttacag attggctcaa attatctttg agaaatttta    4020
tactccaatc ttcattcaag aacctttcac ttcaactcaa caaggttctt caaattttgg    4080
cagtacagct aaacctctac aaatcacaga aaatatagag gttatgtctg aaacagttgc    4140
aaatcaggtt gcaaaatcta gtgtgctacc acgattatat tccattcaag cacatattca    4200
tattgcacca gatattgtta tttctacaac tgccatcatt gatacaggag caacagtctg    4260
ttgtatatct gaaagatag taccagaagc agccaaagaa cagctcaatt acaaagttaa    4320
catttctggt atttcatctc aacagcaaat tcagcataga ctgaaaagag gtacattaga    4380
aattgcatca ataaatatg ctctaccatt gtgttatatc attgaactca atgataaaga    4440
tgattttcct atgattcttg gatgcaattt ctttaaacat atgggggggag gaatgaggtt    4500 tgaaggacct catgttactt tttacaaagg aattactacc ttgagcacct catatgcaaa    4560
tactggtatc gatactgaac atgaacaaat taccagtaca acctctcagt cttttaaaga    4620
aagattttct cccttaatga atgaacttaa agcagcaggc tacattggag aagatcctct    4680
caaacattgg tctaaaaaca aagtcacatg caaattagac ctgaagaata cagagattac    4740
tattcaggat aagcccttaa gacacatcac acctgctctg gaacaatcat atggtcgtca    4800
tgttaatgct ctactcatgc ttaaggttat tcaaccttcc aaaagtagac acagaacaat    4860
ggctttccta gtaaactctg gcaccactgt tacagctgat ggaaaagaaa tcaaaggtaa    4920
agagcgtatg gtctttaatt acaaagccct caatgacaac acctacaaag accaatactc    4980
attaccaaat attcagctta ttttgaaaaa ggtgatcaat agcactatct attctaaatt    5040
tgatctgaaa tctggttttc accaagttgc tatggatccc gattctgtgg aatggacagc    5100
tttcctagtt ccacaaggtt tatatgaatg gctggcaatg ccttttggcc tcaaaaatgc    5160
tccagccgta tttcaaagaa aaatggatgc agtattcaaa gggtgtgaaa aattcctcgc    5220
agtctatatt gatgatattc tggtattttc aaacaatgag gaagatcatg caaaacacct    5280
ggtcatcatg cttcagcggt gtaaagaaca tggtcttgtt cttttcaccta caaaaatgaa    5340 tattgcagtt agagaagtta attttcttgg agccactatt ggcagcagaa aagttaaact    5400
ccaagaaaat attatcaaga agatccttga ctttgataca gagaaacttc aatcaaaaaa    5460
gggtcttcgt tcatttctgg gaattcttaa ctatgcccga atcatattc caaatctcgg    5520 gaaaatagcc ggacctctct attccaaaac ttccatatat ggtgatatca gattttcagc    5580
atctgattgg aagttaatca atgaaatcaa ggctattgtt gagaagctcc caccacttga    5640
ttatcctcca gaacaagcct acatcattat tgaatctgat ggttgtatgg aaggatgggg    5700
cgctatttgt aaatggaagc tcgcagaata tgaccccaag tcaagtgaac aaatttgtgc    5760
gtatgctagt ggtaaattct ctccaatcaa atccactatc gacgcagaaa ttactgccgc    5820
catggaaggg ttagaagcat tcaagatcca ttacttggat aaacaaaaaa taaccctccg    5880
cactgattgc caggcaatca tctcattctg caacaagact tcagtcaaca gccttcacg    5940 ggttagatgg ttgaagttca ttgattatat tactaacact ggaattgatg ttaaatttga    6000
acatattgat gctaaaaata tgtcttagc tgacactctg tccaggttag ttaacacttt    6060
gcaggatttg ccatggctag atgaacctca tcaggatcaa acagtctccc tgatgcagga    6120
aattgaagat gcacctcttg aaatcaagca gcgttcttta acctgcttac agagactgat    6180
ctgtagaagc ttcatggaag attctacaga agaagctatt cacttcctcg aagatgataa    6240
```

```
gatcgagcca acagctgagt catcaacccc aattactttg gatgaattttt caagaaaaag      6300 attccaagaa catacagatc tcttagaaga atttcaatta actttgcttc aaattaatct      6360
tcttgaagca tctcttcatg aacgattaat gaaatgccaa agttatgcaa cgagagataa      6420
tttctgggga gattggctgc ctgaagctcg cagagatctt ttgcaaattc aactagccaa      6480
agaaatcatc gagaaggttc gtgaaaagct tcactctatc tag                        6523
```

<210> SEQ ID NO 2
<211> LENGTH: 7458
<212> TYPE: DNA
<213> ORGANISM: Taro bacilliform virus

<400> SEQUENCE: 2

```
tggtatcaga gctatggtga tgttttctat ggctatggca gcgtaaactt cttctgctca        60
agagggaagt ctaccatgtc ttttatttgc tgatgcaact tcatttaatt tgcctatatt       120
ttgtttgata tatctcatta tttgtaagcc tcgtacttac agtacagacc gataacataa       180
ggtaagctaa ggtagcaggc aaaagaggga acaaagtagc cgcaggagaa aggcgaagaa       240
gtaccgtgag tcttctaccc gaaacttact aagtgttatt tctatctggg atagtttagg       300
tcttggaaaa taatgcgacc ttacaattat atgatttata tcacatttta tggcaaagaa       360
atttgaagca gctattaaag actggtatga taactctcga cgagcagatc tttcctatct       420
tgacctagcc accactacaa aaccttctgc atcacaatta gctcataatc tacaagtcat       480
ttttgataga ttatccttac attcttcagt ctccattaag gaacattacg aagtagttag       540
caaacttcat tctttggaaa aatctataga agaattaaag tctgaattga ctacggtcaa       600
aagggcttta acttctatcc aaaaagaagt tttcacccac aaaccccctca cagcacagga      660 agtgcaaacc cttgcacaaa gtctgatcaa agaacctaag caaatagaac agcaggccgt       720
atttcttcta aaggagctta agaacaaac agcaaaaatt caagctttgc tccacgagct       780
taaaagttga tgtctgtacc taattccaca tacccagggt acatcaaaag tttagaagaa       840
acaaaagtct taggagatcc atctgtagga ttctctgaaa ttcctaccac tgctatcgga       900
accgctacag gttttcaac tctttataag cagaacaata caatcatcaa tctgcttata       960
tctcttcata aaaggttga tagcctctcc aaaaagacag acgtcgacga gttagccact      1020
gagttgtcca aactcacaat caaggatacc ccaaaggtta aggctaaaac tcctctatac      1080
gtcttcaaga gtccccgtct tatcctcgaa gaggaaagat ataaaatcgg ccttcctcct      1140
accactaccg attggacttg gcctgtagga catcctttg ctcctccacc aaaaacatcc       1200
acaaaggcat ccacctcttc ttaaagatgt ctttagcagt tcgtgatcgt ggttccaacc      1260
cttccacctc ttctacagtc cctagtcagc aggaccagat tcgggattat agaaacatgc      1320
aaagagttcg tcatacagcg gaaagagcag caaggagaat cttccctgga agattcaata      1380
gaactctgga atcacaaatc aatccagagg cagaaatccg tctttctcaa caagacgag       1440 cagcaatggt cccagcagaa gtattataca atacttctcc atcaacaaga aatcagaaag      1500
tgtatcagca ctattctgaa gaaagaattc tttgtacagg acaaaatcag caattaaatt      1560
tgccatttat taatgaatct tcttacagag ccctcagaga atcaggtcaa cagcatcttc      1620
acataggcct gatcatgatt cgtgtacatc ctcttcatcg gcgaaatgca ggaacgacag      1680
ctcttattgt ccctcgagac ataagatgga atgatgacag atctatcatt ggcaccatgg      1740
agatagatct cagcgccgga tcccaaattg tttatattgc cccaaatatc atgctatctg      1800
```

```
ttgaagattt ttatcgcaac atacaacttg cgattcaaac tcagggctat gaaaactgga    1860
actctgccga gagtaacttg ctcatctctc gcgctcttat tggtcgtctg acaaacgaca    1920
gttttacagg attccagtac aatatctcta atgttgctga gtacttgcac agtcatggtg    1980
tgcaagctat tgaaggacaa gctcatccaa gaaccctcgg caatcgatgg atcctacaag    2040
caccagcacc accaaggtct ctcgttccac aaaacgtgga gaccaccact cttctggatg    2100
gtaatgtgtc tatacgtttc tccaattacc atcaagcacc agttaatgat actcaggata    2160
attctcatcc tgatatccaa gaagacgaaa accaattcat tggttttctt tctgatttgg    2220
gggaagaata tgaattggag tatccttctt tcactccagt tcatgcagat gaattcattt    2280
ttataatcat taatggggaa gaaattcccg atgattttgt ctcatctttt tgttccaatt    2340
tctctcctcc accaattcca gaaccagaac ccacagccat tgaagaaaca gcttttactt    2400
tggaagaaca attcaatgac ctggactatc ctaccctcat ttcaatggaa aaacaattag    2460
tccagtcttc agttacttca gcttacaacc cacccacaga acctcttatg ggtcaggtag    2520
tctatccacc agcatctgca cctagaccac aagctgaaac ttcttcaacc tctgaaagat    2580
tcaaaaattt cagagcaaag ccatatagta ccccgactat tttcctacct ccagcataca    2640
atcaacaagg ggctatatta gttcttcctg atgacattgg cttatatgaa gataccattt    2700
ctcgttggga gtccattact ctcaacatga tgaatgaaaa ggtttggcca tcaaatgaag    2760
caaaggccaa atatatggaa aatctcttag gagaaatgga gaagaagaca tggatacaat    2820
ggaggaccac atatgtatcc gaatatgatg ctttggtcca acaaagtgat gaaacacaga    2880
acctcctgtc tcaggtaagg aggatatttc tgctacaaga cccatatcaa ggatcaactg    2940
cggaacaaga tcaggcatat aatgatcttg aaagaatttc ttgtgataat attaaggatt    3000
taattcctta tctgattcag ttccgcaatt tagctgcaaa atctggacgc ttgttcttag    3060
gtccagaatt atctgaaaaa ttattcagaa aaatgccgcc tctaataggc aaagaaattg    3120
aaacagcatt catagcaaag catggtaatg caaacatcac tgttatgcct cgcattcatt    3180
ttgcttacca ttatcttgct gaattatgta aaaaggcagc attacagaga tcattgaagg    3240
atctcagctt ctgcaaccag attcctctcc caggaatcta tacaaaaggc aacaagaagt    3300
ttggtcttcg aaaggccaga acatacaaag gaaaaccaca tccaacacat gtacgggtat    3360
tcaaaaaggc aaaataccag cgtacaaaga agtgcaaatg ctttatatgt ggtgaaccag    3420
gacattttgc tcgagaatgc acaaagcaaa gaggaaatat tgtacgagca acagtacatc    3480
aagaactggc cataccagat aatttttgatg ttgtttctgt ggatgcagat gaatctgaca    3540
gctctggcat ctacagttat tcggaaaatg aagctcctct gcaagaagta aattctttca    3600
ttcatgatga aaatatcttt ttcctatctg atgcagacga gtttgaaagc ccacaacagc    3660
atcttcatga aacggtaaat atgcttcaat ctagatctgc ttatttacct caagtagctg    3720
ttggagaaga aaaattgaat tgtagtcaca tttggctaca agatgttgat attccatctg    3780
ataagcacaa atgccacaca tgtagaagag acactcagaa acattacaga ctggaatgtc    3840
aaaaatgcaa attcttggtt tgctcactat gcacaattcc atatctcgga atcaccatgc    3900
aattcaggca aaagcaaaaa tctcagcctg aaaacccaaa cttagtccga gaattgttag    3960
aacatgccat ttttctagaa gaaaaatgca aaaatcaaga attactgtca gaaactcaga    4020
tagaaaggat agtcagttct gaaaaacaag tcaaattttta tggcatccctt cctacaaaaa    4080 agtccaacaa atctgctggg tatgacttac aatccaacat tgatatagaa atcccgccag    4140
gaaaatgtac agtcatttct actggaacct ttctacaaat gcctgacaac atgtatggta    4200
```

```
gacttgtaga aagaacatct ttggcaatac aggggattac agtacaagga ggagtcattg    4260
acccagactt cacaggagaa atacagattg ttctcttcaa tcataatact gctccttatc    4320
ctgtgaagaa aacttacaga ttggctcaaa ttatctttga gaaattttat actccaatct    4380
tcattcaaga acctttcact tcaactcaac aaggttcttc aaattttggc agtacagcta    4440
aacctctaca aatcacagaa aatatagagg ttatgtctga aacagttgca aatcaggttg    4500
caaaatctag tgtgctacca cgattatatt ccattcaagc acatattcat attgcaccag    4560
atattgttat ttctacaact gccatcattg atacaggagc aacagtctgt tgtatatctg    4620
aaaagatagt accagaagca gccaagaac agctcaatta caaagttaac atttctggta    4680
tttcatctca acagcaaatt cagcatagac tgaaaagagg tacattagaa attgcatcaa    4740
ataaatatgc tctaccattg tgttatatca ttgaactcaa tgataaagat gatttttcta    4800
tgattcttgg atgcaatttc tttaaacata tgggggagg aatgaggttt gaaggacctc    4860
atgttacttt ttacaaagga attactacct tgagcacctc atatgcaaat actggtatcg    4920
atactgaaca tgaacaaatt accagtacaa cctctcagtc tttaaagaa agattttctc    4980 ccttaatgaa tgaacttaaa gcagcaggct acattggaga agatcctctc aaacattggt    5040
ctaaaaacaa agtcacatgc aaattagacc tgaagaatac agagattact attcaggata    5100
agcccttaag acacatcaca cctgctctgg aacaatcata tggtcgtcat gttaatgctc    5160
tactcatgct taaggttatt caaccttcca aaagtagaca cagaacaatg ctttcctag    5220 taaactctgg caccactgtt acagctgatg gaaaagaaat caaggtaaa agcgtatgg    5280 tctttaatta caaagccctc aatgacaaca cctacaaaga ccaatactca ttaccaaata    5340
ttcagcttat tttgaaaaag gtgatcaata gcactatcta ttctaaattt gatctgaaat    5400
ctggttttca ccaagttgct atggatcccg attctgtgga atggacagct ttcctagttc    5460
cacaaggttt atatgaatgg ctggcaatgc cttttggcct caaaaatgct ccagccgtat    5520
ttcaaagaaa aatggatgca gtattcaaag ggtgtgaaaa attcctcgca gtctatattg    5580
atgatattct ggtattttca aacaatgagg aagatcatgc aaaacacctg gtcatcatgc    5640
ttcagcggtg taaagaacat ggtcttgttc tttcacctac aaaaatgaat attgcagtta    5700
gagaagttaa ttttcttgga gccactattg gcagcagaaa agttaaactc aagaaaata    5760 ttatcaagaa gatccttgac tttgatacag agaaacttca atcaaaaaag ggtcttcgtt    5820
catttctggg aattcttaac tatgcccgaa atcatattcc aaatctcggg aaaatagccg    5880
gacctctcta ttccaaaact tccatatatg gtgatatcag attttcagca tctgattgga    5940
agttaatcaa tgaaatcaag gctattgttg agaagctccc accacttgat tatcctccag    6000
aacaagccta catcattatt gaatctgatg gttgtatgga aggatgggc gctatttgta    6060 aatggaagct cgcagaatat gaccccaagt caagtgaaca atttgtgcg tatgctagtg    6120 gtaaattctc tccaatcaaa tccactatcg acgcagaaat tactgccgcc atggaagggt    6180
tagaagcatt caagatccat tacttggata aacaaaaaat aaccctccgc actgattgcc    6240
aggcaatcat ctcattctgc aacaagactt cagtcaacaa gccttcacgg ttagatggt    6300 tgaagttcat tgattatatt actaacactg gaattgatgt taaatttgaa catattgatg    6360
ctaaaaataa tgtcttagct gacactctgt ccaggttagt taacactttg caggatttgc    6420
catggctaga tgaacctcat caggatcaaa cagtctccct gatgcaggaa attgaagatg    6480
cacctcttga aatcaagcag cgttctttaa cctgcttaca gagactgatc tgtagaagct    6540
```

-continued

```
tcatggaaga ttctacagaa gaagctattc acttcctcga agatgataag atcgagccaa    6600
cagctgagtc atcaaccccca attactttgg atgaattttc aagaaaaaga ttccaagaac    6660
atacagatct cttagaagaa tttcaattaa ctttgcttca aattaatctt cttgaagcat    6720
ctcttcatga acgattaatg aaatgccaaa gttatgcaac gagagataat ttctggggag    6780
attggctgcc tgaagctcgc agagatcttt tgcaaattca actagccaaa gaaatcatcg    6840
agaaggttcg tgaaaagctt cactctatct agataggatt ctttgtgtgt gagtggcgca    6900
cttgcgcata atgtagtaag gaattattgt acttttacgc tggacgccac taggctccat    6960
gctttctgta atgtcacatc acttttacga attgagcctc ggggagccgt tcgtacaaag    7020
tagatgcttt tctagtcaca tctgactttt ctaaaagcag atgccatcaa ctttattcga    7080
gttgagcctc ggggagccgc tcgtttaaag atgctctttt gaaaatgaca gcgcgtggtg    7140
cgatgtcatt ctcacctttt ctttaatgcg tcggccaccg actgcattat tgagattctc    7200
ttatcccttt gccacctcat cggttgcatt attgggattt cgtatcgagt cgagggacga    7260
ggcctccact actcctataa aaggacctca acccctcaga agaacggcaa gccggaaaca    7320
ccgaacttcc cattcttctc ttgagtcttt cctttgagct tgagcttgtg tgtaatcttt    7380
catagtttct aagtctccga agaacgagca ccgtctcgtg aaggagccga tccttttcca    7440
accacacttt ttctacct                                                  7458
```

<210> SEQ ID NO 3
<211> LENGTH: 146
<212> TYPE: PRT
<213> ORGANISM: Taro bacilliform virus

<400> SEQUENCE: 3

Met Ala Lys Lys Phe Glu Ala Ala Ile Lys Asp Trp Tyr Asp Asn Ser
1               5                   10                  15

Arg Arg Ala Asp Leu Ser Tyr Leu Asp Leu Ala Thr Thr Thr Lys Pro
            20                  25                  30

Ser Ala Ser Gln Leu Ala His Asn Leu Gln Val Ile Phe Asp Arg Leu
        35                  40                  45

Ser Leu His Ser Ser Val Ser Ile Lys Glu His Tyr Glu Val Val Ser
    50                  55                  60

Lys Leu His Ser Leu Glu Lys Ser Ile Glu Glu Leu Lys Ser Glu Leu
65                  70                  75                  80

Thr Thr Val Lys Arg Ala Leu Thr Ser Ile Gln Lys Glu Val Phe Thr
                85                  90                  95

His Lys Pro Leu Thr Ala Gln Glu Val Gln Thr Leu Ala Gln Ser Leu
            100                 105                 110

Ile Lys Glu Pro Lys Gln Ile Glu Gln Gln Ala Val Phe Leu Leu Lys
        115                 120                 125

Glu Leu Lys Glu Gln Thr Ala Lys Ile Gln Ala Leu Leu His Glu Leu
    130                 135                 140

Lys Ser
145

<210> SEQ ID NO 4
<211> LENGTH: 144
<212> TYPE: PRT
<213> ORGANISM: Taro bacilliform virus

<400> SEQUENCE: 4

Met Ser Val Pro Asn Ser Thr Tyr Pro Gly Tyr Ile Lys Ser Leu Glu

-continued

```
1               5                   10                  15

Glu Thr Lys Val Leu Gly Asp Pro Ser Val Gly Phe Ser Glu Ile Pro
            20                  25                  30

Thr Thr Ala Ile Gly Thr Ala Thr Gly Phe Ser Thr Leu Tyr Lys Gln
        35                  40                  45

Asn Asn Thr Ile Ile Asn Leu Leu Ile Ser Leu His Lys Lys Val Asp
    50                  55                  60

Ser Leu Ser Lys Lys Thr Asp Val Asp Glu Leu Ala Thr Glu Leu Ser
65                  70                  75                  80

Lys Leu Thr Ile Lys Asp Thr Pro Lys Val Lys Ala Lys Thr Pro Leu
                85                  90                  95

Tyr Val Phe Lys Ser Pro Arg Leu Ile Leu Glu Glu Glu Arg Tyr Lys
            100                 105                 110

Ile Gly Leu Pro Pro Thr Thr Thr Asp Trp Thr Trp Pro Val Gly His
        115                 120                 125

Pro Phe Ala Pro Pro Pro Lys Thr Ser Thr Lys Ala Ser Thr Ser Ser
    130                 135                 140

<210> SEQ ID NO 5
<211> LENGTH: 1881
<212> TYPE: PRT
<213> ORGANISM: Taro bacilliform virus

<400> SEQUENCE: 5

Met Ser Leu Ala Val Arg Asp Arg Gly Ser Asn Pro Ser Thr Ser Ser
1               5                   10                  15

Thr Val Pro Ser Gln Gln Asp Gln Ile Arg Asp Tyr Arg Asn Met Gln
            20                  25                  30

Arg Val Arg His Thr Ala Glu Arg Ala Ala Arg Arg Ile Phe Pro Gly
        35                  40                  45

Arg Phe Asn Arg Thr Leu Glu Ser Gln Ile Asn Pro Glu Ala Glu Ile
    50                  55                  60

Arg Leu Ser Gln Gln Arg Arg Ala Ala Met Val Pro Ala Glu Val Leu
65                  70                  75                  80

Tyr Asn Thr Ser Pro Ser Thr Arg Asn Gln Lys Val Tyr Gln His Tyr
                85                  90                  95

Ser Glu Glu Arg Ile Leu Cys Thr Gly Gln Asn Gln Gln Leu Asn Leu
            100                 105                 110

Pro Phe Ile Asn Glu Ser Ser Tyr Arg Ala Leu Arg Glu Ser Gly Gln
        115                 120                 125

Gln His Leu His Ile Gly Leu Ile Met Ile Arg Val His Pro Leu His
    130                 135                 140

Arg Arg Asn Ala Gly Thr Thr Ala Leu Ile Val Pro Arg Asp Ile Arg
145                 150                 155                 160

Trp Asn Asp Asp Arg Ser Ile Ile Gly Thr Met Glu Ile Asp Leu Ser
                165                 170                 175

Ala Gly Ser Gln Ile Val Tyr Ile Ala Pro Asn Ile Met Leu Ser Val
            180                 185                 190

Glu Asp Phe Tyr Arg Asn Ile Gln Leu Ala Ile Gln Thr Gln Gly Tyr
        195                 200                 205

Glu Asn Trp Asn Ser Ala Glu Ser Asn Leu Leu Ile Ser Arg Ala Leu
    210                 215                 220

Ile Gly Arg Leu Thr Asn Asp Ser Phe Thr Gly Phe Gln Tyr Asn Ile
225                 230                 235                 240

```
Ser Asn Val Ala Glu Tyr Leu His Ser His Gly Val Gln Ala Ile Glu
            245                 250                 255

Gly Gln Ala His Pro Arg Thr Leu Gly Asn Arg Trp Ile Leu Gln Ala
        260                 265                 270

Pro Ala Pro Arg Ser Leu Val Pro Gln Asn Val Glu Thr Thr Thr
    275                 280                 285

Leu Leu Asp Gly Asn Val Ser Ile Arg Phe Ser Asn Tyr His Gln Ala
290                 295                 300

Pro Val Asn Asp Thr Gln Asp Asn Ser His Pro Asp Ile Gln Glu Asp
305                 310                 315                 320

Glu Asn Gln Phe Ile Gly Phe Leu Ser Asp Leu Gly Glu Glu Tyr Glu
                325                 330                 335

Leu Glu Tyr Pro Ser Phe Thr Pro Val His Ala Asp Glu Phe Ile Phe
            340                 345                 350

Ile Ile Ile Asn Gly Glu Glu Ile Pro Asp Asp Phe Val Ser Ser Phe
        355                 360                 365

Cys Ser Asn Phe Ser Pro Pro Ile Pro Gly Pro Glu Pro Thr Ala
    370                 375                 380

Ile Glu Glu Thr Ala Phe Thr Leu Glu Glu Gln Phe Asn Asp Leu Asp
385                 390                 395                 400

Tyr Pro Thr Leu Ile Ser Met Glu Lys Gln Leu Val Gln Ser Ser Val
                405                 410                 415

Thr Ser Ala Tyr Asn Pro Pro Thr Glu Pro Leu Met Gly Gln Val Val
            420                 425                 430

Tyr Pro Pro Ala Ser Ala Pro Arg Pro Gln Ala Glu Thr Ser Ser Thr
        435                 440                 445

Ser Glu Arg Phe Lys Asn Phe Arg Ala Lys Pro Tyr Ser Thr Pro Thr
    450                 455                 460

Ile Phe Leu Pro Pro Ala Tyr Asn Gln Gln Gly Ala Ile Leu Val Leu
465                 470                 475                 480

Pro Asp Asp Ile Gly Leu Tyr Glu Asp Thr Ile Ser Arg Trp Glu Ser
                485                 490                 495

Ile Thr Leu Asn Met Met Asn Glu Lys Val Trp Pro Ser Asn Glu Ala
            500                 505                 510

Lys Ala Lys Tyr Met Glu Asn Leu Leu Gly Glu Met Glu Lys Lys Thr
        515                 520                 525

Trp Ile Gln Trp Arg Thr Thr Tyr Val Ser Glu Tyr Asp Ala Leu Val
    530                 535                 540

Gln Gln Ser Asp Glu Thr Gln Asn Leu Leu Ser Gln Val Arg Arg Ile
545                 550                 555                 560

Phe Leu Leu Gln Asp Pro Tyr Gln Gly Ser Thr Ala Glu Gln Asp Gln
                565                 570                 575

Ala Tyr Asn Asp Leu Glu Arg Ile Ser Cys Asp Asn Ile Lys Asp Leu
            580                 585                 590

Ile Pro Tyr Leu Ile Gln Phe Arg Asn Leu Ala Ala Lys Ser Gly Arg
        595                 600                 605

Leu Phe Leu Gly Pro Glu Leu Ser Glu Lys Leu Phe Arg Lys Met Pro
    610                 615                 620

Pro Leu Ile Gly Lys Glu Ile Glu Thr Ala Phe Ile Ala Lys His Gly
625                 630                 635                 640

Asn Ala Asn Ile Thr Val Met Pro Arg Ile His Phe Ala Tyr His Tyr
                645                 650                 655

Leu Ala Glu Leu Cys Lys Lys Ala Ala Leu Gln Arg Ser Leu Lys Asp
```

```
                660             665             670
Leu Ser Phe Cys Asn Gln Ile Pro Leu Pro Gly Ile Tyr Thr Lys Gly
        675                 680             685
Asn Lys Lys Phe Gly Leu Arg Lys Ala Arg Thr Tyr Lys Gly Lys Pro
        690                 695             700
His Pro Thr His Val Arg Val Phe Lys Lys Ala Lys Tyr Gln Arg Thr
705             710             715                 720
Lys Lys Cys Lys Cys Phe Ile Cys Gly Glu Pro Gly His Phe Ala Arg
                725             730             735
Glu Cys Thr Lys Gln Arg Gly Asn Ile Val Arg Ala Thr Val His Gln
            740             745             750
Glu Leu Ala Ile Pro Asp Asn Phe Asp Val Val Ser Val Asp Ala Asp
        755             760             765
Glu Ser Asp Ser Ser Gly Ile Tyr Ser Tyr Ser Glu Asn Glu Ala Pro
    770             775             780
Leu Gln Glu Val Asn Ser Phe Ile His Asp Glu Asn Ile Phe Phe Leu
785             790             795                 800
Ser Asp Ala Asp Glu Phe Glu Ser Pro Gln Gln His Leu His Glu Thr
                805             810             815
Val Asn Met Leu Gln Ser Arg Ser Ala Tyr Leu Pro Gln Val Ala Val
                820             825             830
Gly Glu Glu Lys Leu Asn Cys Ser His Ile Trp Leu Gln Asp Val Asp
            835             840             845
Ile Pro Ser Asp Lys His Lys Cys His Thr Cys Arg Arg Asp Thr Gln
        850             855             860
Lys His Tyr Arg Leu Glu Cys Gln Lys Cys Lys Phe Leu Val Cys Ser
865             870             875                 880
Leu Cys Thr Ile Pro Tyr Leu Gly Ile Thr Met Gln Phe Arg Gln Lys
                885             890             895
Gln Lys Ser Gln Pro Glu Asn Pro Asn Leu Val Arg Glu Leu Leu Glu
                900             905             910
His Ala Ile Phe Leu Glu Glu Lys Cys Lys Asn Gln Glu Leu Leu Ser
            915             920             925
Glu Thr Gln Ile Glu Arg Ile Val Ser Ser Glu Lys Gln Val Lys Phe
        930             935             940
Tyr Gly Ile Leu Pro Thr Lys Lys Ser Asn Lys Ser Ala Gly Tyr Asp
945             950             955                 960
Leu Gln Ser Asn Ile Asp Ile Glu Ile Pro Pro Gly Lys Cys Thr Val
                965             970             975
Ile Ser Thr Gly Thr Phe Leu Gln Met Pro Asp Asn Met Tyr Gly Arg
            980             985             990
Leu Val Glu Arg Thr Ser Leu Ala Ile Gln Gly Ile Thr Val Gln Gly
        995             1000            1005
Gly Val Ile Asp Pro Asp Phe Thr Gly Glu Ile Gln Ile Val Leu Phe
    1010            1015            1020
Asn His Asn Thr Ala Pro Tyr Pro Val Lys Lys Thr Tyr Arg Leu Ala
1025            1030            1035                1040
Gln Ile Ile Phe Glu Lys Phe Tyr Thr Pro Ile Phe Ile Gln Glu Pro
                1045            1050            1055
Phe Thr Ser Thr Gln Gln Gly Ser Ser Asn Phe Gly Ser Thr Ala Lys
            1060            1065            1070
Pro Leu Gln Ile Thr Glu Asn Ile Glu Val Met Ser Glu Thr Val Ala
        1075            1080            1085
```

```
Asn Gln Val Ala Lys Ser Ser Val Leu Pro Arg Leu Tyr Ser Ile Gln
    1090            1095                1100

Ala His Ile His Ile Ala Pro Asp Ile Val Ile Ser Thr Thr Ala Ile
1105            1110            1115                1120

Ile Asp Thr Gly Ala Thr Val Cys Cys Ile Ser Glu Lys Ile Val Pro
            1125            1130                1135

Glu Ala Ala Lys Glu Gln Leu Asn Tyr Lys Val Asn Ile Ser Gly Ile
        1140                1145                1150

Ser Ser Gln Gln Gln Ile Gln His Arg Leu Lys Arg Gly Thr Leu Glu
    1155            1160                1165

Ile Ala Ser Asn Lys Tyr Ala Leu Pro Leu Cys Tyr Ile Ile Glu Leu
1170            1175                1180

Asn Asp Lys Asp Asp Phe Ser Met Ile Leu Gly Cys Asn Phe Lys
1185            1190                1195                1200

His Met Gly Gly Gly Met Arg Phe Glu Gly Pro His Val Thr Phe Tyr
            1205                1210                1215

Lys Gly Ile Thr Thr Leu Ser Thr Ser Tyr Ala Asn Thr Gly Ile Asp
        1220                1225                1230

Thr Glu His Glu Gln Ile Thr Ser Thr Thr Ser Gln Ser Phe Lys Glu
    1235            1240                1245

Arg Phe Ser Pro Leu Met Asn Glu Leu Lys Ala Ala Gly Tyr Ile Gly
    1250            1255                1260

Glu Asp Pro Leu Lys His Trp Ser Lys Asn Lys Val Thr Cys Lys Leu
1265            1270                1275                1280

Asp Leu Lys Asn Thr Glu Ile Thr Ile Gln Asp Lys Pro Leu Arg His
        1285            1290                1295

Ile Thr Pro Ala Leu Glu Gln Ser Tyr Gly Arg His Val Asn Ala Leu
        1300            1305                1310

Leu Met Leu Lys Val Ile Gln Pro Ser Lys Ser Arg His Arg Thr Met
    1315            1320                1325

Ala Phe Leu Val Asn Ser Gly Thr Thr Val Thr Ala Asp Gly Lys Glu
    1330            1335                1340

Ile Lys Gly Lys Glu Arg Met Val Phe Asn Tyr Lys Ala Leu Asn Asp
1345            1350                1355                1360

Asn Thr Tyr Lys Asp Gln Tyr Ser Leu Pro Asn Ile Gln Leu Ile Leu
        1365            1370                1375

Lys Lys Val Ile Asn Ser Thr Ile Tyr Ser Lys Phe Asp Leu Lys Ser
        1380            1385                1390

Gly Phe His Gln Val Ala Met Asp Pro Asp Ser Val Glu Trp Thr Ala
    1395            1400                1405

Phe Leu Val Pro Gln Gly Leu Tyr Glu Trp Leu Ala Met Pro Phe Gly
    1410            1415                1420

Leu Lys Asn Ala Pro Ala Val Phe Gln Arg Lys Met Asp Ala Val Phe
1425            1430                1435                1440

Lys Gly Cys Glu Lys Phe Leu Ala Val Tyr Ile Asp Asp Ile Leu Val
            1445            1450                1455

Phe Ser Asn Asn Glu Glu Asp His Ala Lys His Leu Val Ile Met Leu
        1460            1465                1470

Gln Arg Cys Lys Glu His Gly Leu Val Leu Ser Pro Thr Lys Met Asn
            1475            1480                1485

Ile Ala Val Arg Glu Val Asn Phe Leu Gly Ala Thr Ile Gly Ser Arg
    1490            1495                1500
```

```
Lys Val Lys Leu Gln Glu Asn Ile Ile Lys Lys Ile Leu Asp Phe Asp
1505                1510                1515                1520

Thr Glu Lys Leu Gln Ser Lys Lys Gly Leu Arg Ser Phe Leu Gly Ile
            1525                1530                1535

Leu Asn Tyr Ala Arg Asn His Ile Pro Asn Leu Gly Lys Ile Ala Gly
        1540                1545                1550

Pro Leu Tyr Ser Lys Thr Ser Ile Tyr Gly Asp Ile Arg Phe Ser Ala
    1555                1560                1565

Ser Asp Trp Lys Leu Ile Asn Glu Ile Lys Ala Ile Val Glu Lys Leu
1570                1575                1580

Pro Pro Leu Asp Tyr Pro Pro Glu Gln Ala Tyr Ile Ile Ile Glu Ser
1585                1590                1595                1600

Asp Gly Cys Met Glu Gly Trp Gly Ala Ile Cys Lys Trp Lys Leu Ala
            1605                1610                1615

Glu Tyr Asp Pro Lys Ser Ser Glu Gln Ile Cys Ala Tyr Ala Ser Gly
        1620                1625                1630

Lys Phe Ser Pro Ile Lys Ser Thr Ile Asp Ala Glu Ile Thr Ala Ala
    1635                1640                1645

Met Glu Gly Leu Glu Ala Phe Lys Ile His Tyr Leu Asp Lys Gln Lys
1650                1655                1660

Ile Thr Leu Arg Thr Asp Cys Gln Ala Ile Ile Ser Phe Cys Asn Lys
1665                1670                1675                1680

Thr Ser Val Asn Lys Pro Ser Arg Val Arg Trp Leu Lys Phe Ile Asp
            1685                1690                1695

Tyr Ile Thr Asn Thr Gly Ile Asp Val Lys Phe Glu His Ile Asp Ala
        1700                1705                1710

Lys Asn Asn Val Leu Ala Asp Thr Leu Ser Arg Leu Val Asn Thr Leu
    1715                1720                1725

Gln Asp Leu Pro Trp Leu Asp Glu Pro His Gln Asp Gln Thr Val Ser
1730                1735                1740

Leu Met Gln Glu Ile Glu Asp Ala Pro Leu Glu Ile Lys Gln Arg Ser
1745                1750                1755                1760

Leu Thr Cys Leu Gln Arg Leu Ile Cys Arg Ser Phe Met Glu Asp Ser
            1765                1770                1775

Thr Glu Glu Ala Ile His Phe Leu Glu Asp Asp Lys Ile Glu Pro Thr
        1780                1785                1790

Ala Glu Ser Ser Thr Pro Ile Thr Leu Asp Glu Phe Ser Arg Lys Arg
    1795                1800                1805

Phe Gln Glu His Thr Asp Leu Leu Glu Glu Phe Gln Leu Thr Leu Leu
1810                1815                1820

Gln Ile Asn Leu Leu Glu Ala Ser Leu His Glu Arg Leu Met Lys Cys
1825                1830                1835                1840

Gln Ser Tyr Ala Thr Arg Asp Asn Phe Trp Gly Asp Trp Leu Pro Glu
            1845                1850                1855

Ala Arg Arg Asp Leu Leu Gln Ile Gln Leu Ala Lys Glu Ile Ile Glu
        1860                1865                1870

Lys Val Arg Glu Lys Leu His Ser Ile
    1875                1880

<210> SEQ ID NO 6
<211> LENGTH: 1190
<212> TYPE: DNA
<213> ORGANISM: Taro bacilliform virus

<400> SEQUENCE: 6
```

```
gccttcacgg gttagatggt tgaagttcat tgattatatt actaacactg gaattgatgt      60
taaatttgaa catattgatg ctaaaaataa tgtcttagct gacactctgt ccaggttagt     120
taacactttg caggatttgc catggctaga tgaacctcat caggatcaaa cagtctccct     180
gatgcaggaa attgaagatg cacctcttga aatcaagcag cgttctttaa cctgcttaca     240
gagactgatc tgtagaagct tcatggaaga ttctacagaa gaagctattc acttcctcga     300
agatgataag atcgagccaa cagctgagtc atcaacccca attactttgg atgaattttc     360
aagaaaaaga ttccaagaac atacagatct cttagaagaa tttcaattaa ctttgcttca     420
aattaatctt cttgaagcat ctcttcatga acgattaatg aaatgccaaa gttatgcaac     480
gagagataat ttctggggag attggctgcc tgaagctcgc agagatcttt tgcaaattca     540
actagccaaa gaaatcatcg agaaggttcg tgaaaagctt cactctatct agataggatt     600
ctttgtgtgt gagtggcgca cttgcgcata atgtagtaag gaattattgt acttttacgc     660
tggacgccac taggctccat gctttctgta atgtcacatc acttttacga attgagcctc     720
ggggagccgt tcgtacaaag tagatgcttt tctagtcaca tctgactttt ctaaaagcag     780
atgccatcaa cttttattcg agttgagcct cggggagccg ctcgtttaaag atgctctttt    840 gaaaatgaca gcgcgtggtg cgatgtcatt ctcaccttt ctttaatgcg tcggccaccg    900
actgcattat tgagattctc ttatcccttt gccacctcat cggttgcatt attgggattt     960
cgtatcgagt cgagggacga ggcctccact actcctataa aaggacctca accctcaga    1020 agaacggcaa gccggaaaca ccgaacttcc cattcttctc ttgagtcttt cctttgagct    1080
tgagcttgtg tgtaatcttt catagtttct aagtctccga agaacgagca ccgtctcgtg    1140
aaggagccga tcctttccca accacacttt ttctaccttg gtatcagagc                1190

<210> SEQ ID NO 7
<211> LENGTH: 598
<212> TYPE: DNA
<213> ORGANISM: Taro bacilliform virus

<400> SEQUENCE: 7
ataggattct ttgtgtgtga gtggcgcact tgcgcataat gtagtaagga attattgtac      60
ttttacgctg gacgccacta ggctccatgc tttctgtaat gtcacatcac ttttacgaat     120
tgagcctcgg ggagccgttc gtacaaagta gatgcttttc tagtcacatc tgactttct     180 aaaagcagat gccatcaact tattcgagt tgagcctcgg ggagccgctc gtttaaagat     240
gctcttttga aaatgacagc gcgtggtgcg atgtcattct cacctttct ttaatgcgtc     300 ggccaccgac tgcattattg agattctctt atccctttgc cacctcatcg gttgcattat     360
tgggatttcg tatcgagtcg agggacgagg cctccactac tcctataaaa ggacctcaac     420
ccctcagaag aacggcaagc cggaaacacc gaacttccca ttcttctctt gagtctttcc     480
tttgagcttg agcttgtgtg taatctttca gtttctaa gtctccgaag aacgagcacc      540
gtctcgtgaa ggagccgatc cttttccaac cacactttt ctaccttggt atcagagc       598

<210> SEQ ID NO 8
<211> LENGTH: 529
<212> TYPE: DNA
<213> ORGANISM: Taro bacilliform virus

<400> SEQUENCE: 8
ggacgccact aggctccatg ctttctgtaa tgtcacatca cttttacgaa ttgagcctcg

```
gggagccgtt cgtacaaagt agatgctttt ctagtcacat ctgactttc taaaagcaga      120 tgccatcaac tttattcgag ttgagcctcg gggagccgct cgtttaaaga tgctcttttg      180
aaaatgacag cgcgtggtgc gatgtcattc tcaccttttc tttaatgcgt cggccaccga      240
ctgcattatt gagattctct tatccctttg ccacctcatc ggttgcatta ttgggatttc      300
gtatcgagtc gagggacgag gcctccacta ctcctataaa aggacctcaa cccctcagaa      360
gaacggcaag ccggaaacac cgaacttccc attcttctct tgagtctttc ctttgagctt      420
gagcttgtgt gtaatctttc atagtttcta agtctccgaa gaacgagcac cgtctcgtga      480
aggagccgat ccttttccaa ccacactttt tctaccttgg tatcagagc                  529
```

```
<210> SEQ ID NO 9
<211> LENGTH: 261
<212> TYPE: DNA
<213> ORGANISM: Taro bacilliform virus

<400> SEQUENCE: 9
tgccacctca tcggttgcat tattgggatt tcgtatcgag tcgagggacg aggcctccac       60
tactcctata aaaggacctc aacccctcag aagaacggca gccggaaaac accgaacttc      120
ccattcttct cttgagtctt tcctttgagc ttgagcttgt gtgtaatctt tcatagtttc      180
taagtctccg aagaacgagc accgtctcgt gaaggagccg atccttttcc aaccacactt     240
tttctacctt ggtatcagag c                                                 261

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)
<223> OTHER INFORMATION: inosine
<220> FEATURE:
<221> NAME/KEY: modified_base
<222> LOCATION: (12)
<223> OTHER INFORMATION: inosine
<220> FEATURE:
<221> NAME/KEY: modified_base
<222> LOCATION: (21)
<223> OTHER INFORMATION: inosine

<400> SEQUENCE: 10
atgccnttyg gnaaraaygc ncc                                               23

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (10)
<223> OTHER INFORMATION: inosine
<220> FEATURE:
<221> NAME/KEY: modified_base
<222> LOCATION: (13)
<223> OTHER INFORMATION: inosine
<220> FEATURE:
<221> NAME/KEY: modified_base
<222> LOCATION: (16)
<223> OTHER INFORMATION: inosine
```

```
<220> FEATURE:
<221> NAME/KEY: modified_base
<222> LOCATION: (22)
<223> OTHER INFORMATION: inosine

<400> SEQUENCE: 11
ccayttrcan acnscncccc ancc                                            24

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggatgcagta ttcaaagggt gtg                                             23

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctgcaggcgg ccgcgctctg atacca                                          26

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agtctttcct ttgagcttga gc                                              22

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cacacccttt gaatactgca tccat                                           25

<210> SEQ ID NO 16
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tggtatcaga gc                                                         12

<210> SEQ ID NO 17
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 17
ctgcagatag gattctttgt gtgtg                                           25

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccatgggctc tgataccaag gtag                                            24

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctgcagggac gccactaggc                                                 20

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctgcaggcca cctcatcggt tgc                                             23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ctgcaggagc ttgagcttgt gtg                                             23

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ctgcaggcct tcacgggtta gatg                                            24

<210> SEQ ID NO 23
<211> LENGTH: 24
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 23
ggatccgctc tgataccaag gtag                                              24

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ctgcaggggg agattggctg c                                                 21

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ggaagcttgc ggccgccgag aaggttcg                                          28

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcggaagatc ttgctctgat accaaggtag                                        30

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ccatggatca tataattgta aggtcgc                                           27

<210> SEQ ID NO 28
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
atgtttacgt cctgt                                                        15

<210> SEQ ID NO 29
<211> LENGTH: 12
<212> TYPE: DNA
<213> ORGANISM: Artificial Sequence
<220> FEATURE:
<223> OTHER INFORMATION: Description of Artificial Sequence: Synthetic

```
                          primer

<400> SEQUENCE: 29
ttacttgttt gc                                                      12

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide motif
<220> FEATURE:
<221> NAME/KEY: MOD_RES
<222> LOCATION: (2)
<223> OTHER INFORMATION: variable amino acid
<220> FEATURE:
<221> NAME/KEY: MOD_RES
<222> LOCATION: (4)
<223> OTHER INFORMATION: variable amino acid
<220> FEATURE:
<221> NAME/KEY: MOD_RES
<222> LOCATION: (6)
<223> OTHER INFORMATION: variable amino acid

<400> SEQUENCE: 30

Cys Xaa Cys Xaa His Xaa Cys
1               5

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
aaataatgtc ttagctgaca ctc                                          23

<210> SEQ ID NO 32
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tcctataaaa gga                                                     13

<210> SEQ ID NO 33
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tggtatcaga gc                                                      12
```